US007462427B2

(12) United States Patent
Goodby et al.

(10) Patent No.: US 7,462,427 B2
(45) Date of Patent: Dec. 9, 2008

(54) LIQUID CRYSTAL COMPOUNDS WITH BRANCHED OR CYCLIC END GROUPS

(75) Inventors: John W Goodby, Hull (GB); Michael Hird, Hull (GB); Kenneth J Toyne, Hull (GB); Guirec Y Cosquer, Hull (GB); Stephen J Cowling, Hull (GB); Neil Gough, Hull (GB)

(73) Assignee: Qinetiq Limited, London (GB)

( * ) Notice: Subject to any disclaimer, the term of this patent is extended or adjusted under 35 U.S.C. 154(b) by 636 days.

(21) Appl. No.: 10/489,708

(22) PCT Filed: Sep. 12, 2002

(86) PCT No.: PCT/GB02/04183

§ 371 (c)(1),
(2), (4) Date: Apr. 29, 2004

(87) PCT Pub. No.: WO03/024903

PCT Pub. Date: Mar. 27, 2003

(65) Prior Publication Data

US 2004/0206933 A1 Oct. 21, 2004

(30) Foreign Application Priority Data

Sep. 14, 2001 (GB) ................................ 0122190.2

(51) Int. Cl.
*C09K 19/52* (2006.01)
*C09K 19/00* (2006.01)

(52) U.S. Cl. ................. 430/20; 430/270.1; 252/299.01; 252/299.6; 252/299.61; 252/299.62; 252/299.63; 252/299.64; 252/299.65; 252/299.66

(58) Field of Classification Search ............ 252/299.01, 252/299.6, 299.61, 299.62, 299.63, 299.64, 252/299.65, 299.66; 430/270.1
See application file for complete search history.

(56) References Cited

U.S. PATENT DOCUMENTS 3,600,445 A 8/1971 Wirth et al.
4,077,260 A 3/1978 Gray et al.
5,382,380 A 1/1995 Kurihara et al.
5,494,605 A 2/1996 Kurihara et al.
5,750,051 A 5/1998 Goulding et al.
6,030,668 A * 2/2000 Hall et al. .............. 252/299.01

FOREIGN PATENT DOCUMENTS

DE 26 39 838 A 3/1977
EP 0 360 042 A 3/1990
EP 0733692 A1 9/1995
FR 1 488 494 A 7/1967
WO WO 91/03446 A1 3/1991
WO WO 94/27949 A1 12/1994

OTHER PUBLICATIONS

Gray et al; "The Synthesis and Transition Temperatures of Some 4,4"-Dialkyl-and 4-4"-Alkoxyalkyl-1, 1':4',1"-Terphenyls With 2,3- or 2',3'-Difluoro Substituents and of Their Biphenyl Analogues"; J. Chem. Soc. Perkin Trans. II, vol. 12, No. 1989, pp. 2041-2053, XP009001256.

Patent Abstracts of Japan, vol. 1996, No. 01, Jan. 31, 1996 & JP 07 233109 A, Sep. 5, 1995.

Patent Abstracts of Japan, vol. 1996, No. 08, Aug. 30, 1996 & JP 08 092137 A, Apr. 9, 1996.

Gershuni et al; "Effect of Substituents on the Melting Points and Spectroscopic Characteristics of Some Popular Scintillators"; J. Phys. Chem., vol. 84, No. 5, 1980, pp. 517-520, XP001120314.

Patent Abstracts of Japan, vol. 1995, No. 8, Sep. 29, 1995 & JP 07 118241 A, May 9, 1995.

Gray et al; "Mesomorphic Transition Temperatures and Viscosities for Some Cyano-Biphenyls and—P-Terphenyls With Branched Terminal Alkyl Groups"; Mol. Cryst. Liq. Cryst., vol. 104, 1984, pp. 335-345, XP009001155.

Meijere et al; "Liquid Crystalline Bicyclo1.1.1Pentane Derivatives"; Molecular Crystals and Liquid Crystals Science and Technology. Section A. Molecular Crystals and Liquid Crystals, Gordon and Breach Publishers, CH, CH, vol. 257, 1994, pp. 161-167, XP000889813.

(Continued)

*Primary Examiner*—Geraldina Visconti
(74) *Attorney, Agent, or Firm*—Nixon & Vanderhye P.C.

(57) ABSTRACT

The use of a mesogenic compound having a terminal end chain comprising carbon, oxygen, or sulphur, which has at least one pendent $C_{1-4}$alkyl, $C_{1-4}$alkoxy or a cycloalkyl ring, arranged no more than 6 atoms from the end of the chain either decreasing the melting point, increasing the clearing point, increasing the speed of switching and/or increasing the tilt angle of a liquid crystal mixture. Examples of such compounds are of formula (I)

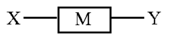

(I)

where M is a mesogenic core group, and X and Y are terminal groups, provided that at least one group X or Y is a group of sub-formula (i)

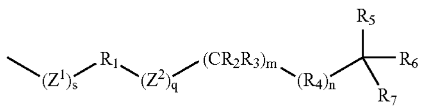

(i)

where $Z^1$, $Z^2$, $R_1$, $R_2$, $R_3$, $R_4$, $R_5$, $R_6$, $R_7$, s, q, m and n are as defined in the specification. Novel compounds of formula (I) are also described and claimed.

9 Claims, 2 Drawing Sheets

OTHER PUBLICATIONS

Patent Abstracts of Japan, vol. 017, No. 659 (C-1137), Dec. 7, 1993 & JP 05 213825 A, Aug. 24, 1993.

Debono et al; "Semisynthetic Chemical Modification of the Antifungal Lipopeptide Echinocandin B (ECB): Structure-Activity Studies of the Lipophilic and Geometric Parameters of Polyarylated Acyl Analogs of ECB" Journal of Medicinal Chemistry, American Chemical Society. Washington, US, vol. 38, No. 17, Aug. 18, 1995, pp. 3271-3281, XP000608473.

Chemical Abstracts, abstr No. 123:302153 & Liq. Cryst., 1995, vol. 19(2), pp. 207-211.

Chemical Abstracts, abstr No. 121:108224 & JP 060058881 A2 Apr. 3, 1994.

Chemical Abstracts, abstr No. 120:149588 & Ferroelectrics, 1993, vol. 138(1-4), pp. 95-101.

Chemical Abstracts, abstr No. 117:161106 & JP 040103555 A2 Jun. 4, 1992.

Chemical Abstracts, abstr No. 124:55499 & J. Med. Cham. 1995, vol. 38(23), pp. 4693-4703.

* cited by examiner

LIQUID CRYSTAL COMPOUNDS WITH BRANCHED OR CYCLIC END GROUPS

This application is the US national phase of international application PCT/GB02/04183 filed in English on 12 Sep. 2002, which designated the US. PCT/GB02/04183 claims priority to GB Application No. 0122190.2 filed 14 Sep. 2001. The entire contents of these applications are incorporated herein by reference.

The present invention relates to novel compounds, which have the properties of liquid crystals, together with processes for their preparation and liquid crystal devices incorporating them.

The term "liquid crystals" is well known. It refers to compounds which, as a result of their structure, will align themselves in a similar orientation, preferably at working temperatures, for example of from −40 to 200° C. These materials are useful in various devices, in particular the liquid crystal display devices or LCDs.

Liquid crystals can exist in various phases. In essence there are three different classes of liquid crystalline material, each possessing a characteristic molecular arrangement. These classes are nematic, chiral nematic (cholesteric) and smectic.

Broadly speaking, the molecules of nematic compounds will align themselves in a particular orientation in a bulk material. Smectic materials, in addition to being orientated in a similar way, will align themselves closely in layers.

A wide range of smectic phases exists, for example smectic A and smectic C. In the former, the molecules are aligned perpendicularly to a base or support, whilst in the latter, molecules may be inclined to the support. Some liquid crystal materials possess a number of liquid crystal phases on varying the temperature. Others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a useful working temperature range.

Such materials are useful, in particular in display devices where their ability to align themselves and to change their alignment under the influence of voltage, is used to impact on the path of polarised light, thus giving rise to liquid crystal displays. These are widely used in devices such as watches, calculators, display boards or hoardings, computer screens, in particular laptop computer screens etc. The properties of the compounds which impact on the speed with which the compounds respond to voltage charges include molecule size, viscosity ($\Delta n$), dipole moments ($\Delta\epsilon$), conductivity etc.

U.S. Pat. Nos. 5,547,604, 5,855,813 and 5,942,155 describe a range of liquid crystal compounds, in particular those which have a smectic phase, and which include siloxanes incorporated into the terminal chains. Siloxanes are generally expensive and difficult to produce. Some liquid crystal compounds with cyclic end groups are described in JP 04103555 and WO 91/03446.

The applicants have found that by introducing bulky end groups into mesogenic compounds, the melting point of the compounds decrease and the clearing points of the compounds increase, leading to a wider temperature range for the liquid crystal phases and so making them useful liquid crystal compounds in the context of liquid crystal mixtures. Furthermore, it is not necessary to include expensive silicon based side chains.

In particular the invention provides the The use of a mesogenic compound having a terminal end chain comprising carbon, oxygen, or sulphur, which has at least one pendent $C_{1-4}$alkyl or $C_{1-4}$alkoxy groups, or a cycloalkyl or cycloalkoxy ring, arranged no more than 6 atoms from the end of the chain for either decreasing the melting point, increasing the clearing point, increasing the speed of switching and/or increasing the tilt angle obtained using a liquid crystal mixture.

In effect, in order to obtain these beneficial effects on the properties of a liquid crystal mixture, it is simply necessary to utilise a compound as defined above as a component or the mixture, or to add such a compound to a pre-existing liquid crystal compound or mixture. Such compounds may suitably be present in the mixtures in an amount of from 3 to 99% w/w and more suitably from 5 to 95% w/w. They have good miscibility with other liquid crystal compounds including other materials which do not have bulky side chains.

The term "pendent" refers to a branched chain structure. Thus pendent groups are attached to the chain at any carbon atom except the terminal carbon atom. Compounds which have at least two pendent $C_{1-4}$alkyl or $C_{1-4}$alkoxy groups are novel and form a further aspect of the invention.

The applicants have found that by including at least one branched chain or bulky group such as a cyclic group at the end of the group, the liquid crystal properties and particularly the Smectic C phase properties of the compounds are improved. Specifically, the compounds show enhanced phase stability, and particularly the Smectic C phase range is increased, as compared to similar compounds which lack the bulky end group.

Particular examples of compounds which may be used in accordance with the the invention are represented by formula (I)

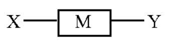

(I)

where M is a mesogenic core group, and X and Y are selected from a functional group, an optionally substituted alkyl chain, an optionally substituted alkenyl chain, an optionally substituted alkynyl chain;

provided that at least one group X or Y is a group of sub-formula (i)

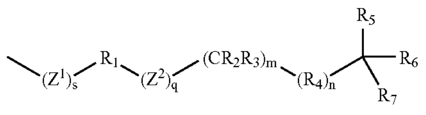

(i)

where $R_1$ is an alkylene chain optionally interposed with one or more oxygen or sulphur atoms;

$Z^1$ and $Z^2$ are independently selected from oxygen or sulphur s and q are independently selected from 0 or 1;

m is 0 or 1;

$R_2$, $R_3$, $R_5$ and $R_6$ are independently selected from hydrogen, $C_{1-4}$alkyl, $C_{1-4}$alkoxy; or $R_5$ and $R_6$ or $R_2$ and $R_3$ together with the carbon atom to which they are attached form a $C_{3-7}$cycloalkyl or $C_{3-7}$cycloalkoxy group, provided that at least one of the groups $R_2$, $R_3$, $R_5$ and $R_6$ is other than hydrogen, n is 0 or an integer of from 1 to 4, and each group $R_4$ is independently selected from oxygen, sulphur or a group $CR_8R_9$ where $R_8$ and $R_9$ are independently selected from hydrogen, $C_{1-4}$alkyl or $C_{1-4}$alkoxy, and $R_7$ is hydrogen or methyl, provided that where $R_7$ is methyl, n is other than 4.

As used herein the term “hydrocarbyl” refers to organic groups comprising carbon and hydrogen atoms such as alkyl, alkenyl, alkynyl, cycloalkyl, aryl or aralkyl. The term “alkyl” refers to straight or branched chain alkyl group, suitably containing up to 20, more suitably up to 10 and preferably up to 6 carbon atoms. The term “alkylene” refers to such groups which are divalent and “cycloalkyl” refers to such groups which have at least 3 carbon atoms, and which are cyclic in structure. The term “alkenyl” or “alkynyl” refers to unsaturated straight or branched chains containing at least 2 carbon atoms, and suitably from 2-20, preferably from 2-10 carbon atoms. The term “aryl” refers to aromatic rings such as phenyl and naphthyl. The term aralkyl refers to alkyl groups substituted by aryl groups such as benzyl.

References to “heterocyclic groups” refer to rings which may be mono or bicyclic and aromatic, non-aromatic or, in the case of bicyclic rings, partially aromatic and partially non-aromatic. These rings suitably contain from 3 to 20 atoms, up to seven of which are heteroatoms selected from oxygen, nitrogen or sulphur.

The term “functional group” as used herein refers to reactive groups such as halo, cyano, nitro, oxo, —$OC(O)R^a$, —$OR^a$, —$C(O)OR^a$, $S(O)_tR^a$, $NR^bR^c$, $OC(O)NR^bR^c$, $C(O)NR^bR^c$, $OC(O)NR^bR^c$, —$NR^7C(O)_nR^6$, —$NR^aCONR^bR^c$, —$C{=}NOR^a$, —$N{=}CR^bR^c$, $S(O)_tNR^bR^c$, $C(S)_nR^a$, $C(S)OR^a$, $C(S)NR^bR^c$ or —$NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_s$, oxygen and nitrogen, n' is an integer of 1 or 2, s is 0, 1 or 2, t is 0 or an integer of 1-3. In particular the functional groups are groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, —$NR^7C(O)_nR^6$, —$NR^aCONR^bR^c$, —$NR^aCSNR^bR^c$, —$C{=}NOR^a$, —$N{=}CR^bR^c$, $S(O)_tNR^bR^c$, or —$NR^bS(O)_tR^a$ where $R^a$, $R^b$ and $R^c$, n and t are as defined above.

Suitable optional substitutents for hydrocarbyl groups $R^a$, $R^b$ and $R^c$ are halo, cyano, nitro, oxo, carboxy or alkyl esters thereof, alkoxy, alkoxycarbonyl, amido, mono or di-alkylamido, amino, mono or di-alkylamino, alkyl sulphonyl, or thioalkyl.

In formula (I), particular functional groups for X or Y are cyano, halo such as fluoro or a group $OR^a$ where $R^a$ is as defined above, and in particular is alkyl.

Suitable optional substitutents for X and Y where these are an optionally substituted alkyl chain, an optionally substituted alkenyl chain, an optionally substituted alkynyl chain are functional groups as defined above. In a preferred embodiment, one of X or Y is a group of sub-formula (i) and the other is alkyl.

Preferably however, both X and Y are groups of sub-formula (i). Such compounds are novel and form a further aspect of the invention.

Preferably, at least two of $R_2$, $R_3$, $R_5$ and $R_6$ are other than hydrogen, and in particular are $C_{1-4}$alkyl groups such as methyl, ethyl or propyl, especially methyl.

Preferably all groups $R_8$ and $R_9$ are hydrogen.

Preferably, $Z^1$ and $Z^2$ where they are present, are oxygen.

In a preferred embodiment, s is 1, q is 0 or 1 and $R_1$ is a group of sub formula (ii)

$$—(CH_2)_p— \qquad (ii)$$

where p is an integer of from 1 to 10, preferably from 2 to 10 and more preferably from 3 to 7.

In an alternative embodiment, s and q are 0 and $R_1$ is a $C_{1-10}$alkylene chain, and preferably a $C_{2-6}$alkylene chain.

Particular examples of groups (i) include groups of sub-formulae (iii), (iv) or (v)

(iii)

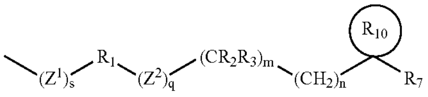

(iv)

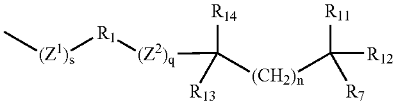

(v)

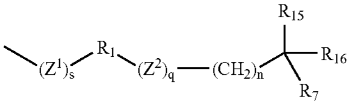

where $Z^1$, $Z^2$, $R_1$, $R_2$, $R_3$, $R_7$, s, q, m and n are as defined in relation to sub-formula (i), $R_{10}$ is a $C_{3-7}$cycloalkyl or $C_{3-7}$cycloalkoxy group, and is preferably a $C_4$cycloalkyl or $C_3$cycloalkoxy group, $R_{11}$ and $R_{12}$ are independently selected from hydrogen or $C_{1-3}$alkyl such as methyl, $R_{13}$ is hydrogen or methyl, $R_{14}$ is $C_{1-3}$alkyl such as methyl, $R_{15}$ is hydrogen or $C_{1-3}$alkyl such as methyl, and $R_{16}$ is $C_{1-3}$alkyl such as methyl.

In particular, the group of sub-formula (i) is a group of sub-formula (iii) where m is 0, since the ring structure provides a good deal of bulk at the end of the chain.

Where the group of sub-formula (i) is a group of sub-formula (iv), $R_{13}$ is suitably hydrogen. $R_{11}$ and $R_{12}$ may both be hydrogen, both be methyl, of one of $R_{11}$ or $R_{12}$ is hydrogen and the other is methyl.

Where the group of sub-formula (i) is a group of sub-formula (v), at least one and preferably both of $R_7$ and $R_{16}$ is methyl.

Examples of groups of formula (iii) are formula (iiia) and (iiib)

(iiia)

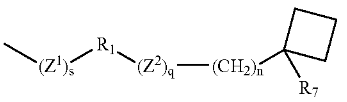

(iiib)

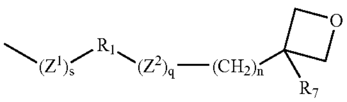

where $Z^1$, $Z^2$, s, q, $R_1$ and $R_7$ are as defined above.

Examples of groups of formula (iv) are groups of sub-formula (iva), (ivb), (ivc), (ivd) or (ive)

(iva)

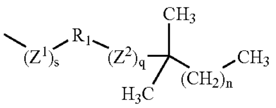

-continued (ivb)

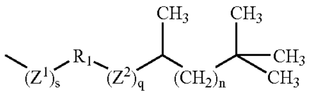

(ivc)

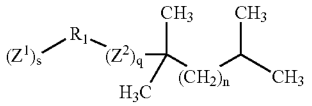

(ivd)

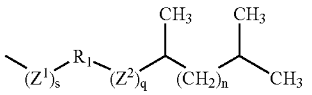

(ive)

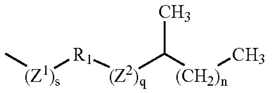

where $Z^1$, $Z^2$, s, q, $R_1$ and n are as defined above.

Suitable mesogenic groups M in formula (I) are known in the art. In particular such groups may be represented by the general formula (II)

$$—(R_{17}—W_1)_f—(R_{18}—W_2)_g—(R_{19})— \quad \text{(II)}$$

where $R_{17}$, $R_{18}$ and $R_{19}$ are independently selected from cycloalkyl, aryl or heterocyclic rings, any of which may be optionally substituted by one or more groups selected from halo $C_{1-5}$alkyl, cyano, $C_{1-5}$alkoxy or NCS;

$W_1$ and $W_2$ are independently selected from a direct bond, —C(O)O—, —OC(O)—, —$CH_2$—, —$CH_2CH_2$—, —$CH_2O$—, —$OCH_2$—, —O—, —S—, —CH═CH—, or —C≡C—;

f is 1 or 2, g is O, 1 or 2, provided that f+g does not exceed 3.

Examples of monocyclic rings for $R_{17}$, $R_{18}$ and $R_{19}$ include any of the following:

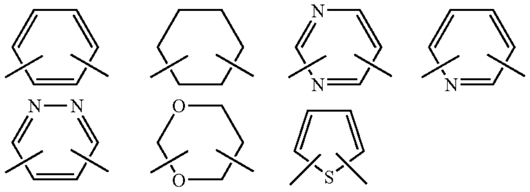

Examples of bicyclic rings for $R_{17}$, $R_{18}$ and $R_{19}$ include for example groups of formula

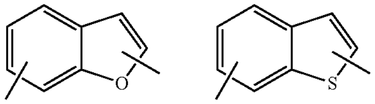

as described for example in International Patent Application no. PCT/GB00/03545; as well as other groups such as

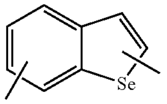

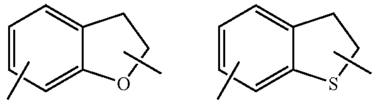

Any of the above rings may carry further substitutents at available bonding points as described above.

In particular however, $R_{17}$, $R_{18}$ and $R_{19}$ are selected from phenyl and cyclohexyl rings, which maybe optionally substituted as described above. In particular, the compound of formula (I) is a group of formula (III)

(III)

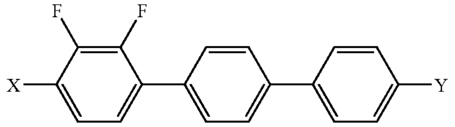

Particular examples of compounds of formula (III) are set out in Table 1.

TABLE 1

| Compound No. | X | Y |
|---|---|---|
| 1 | $C_8H_{17}O$— | —$O(CH_2)_6C(CH_3)_3$ |
| 2 | $C_8H_{17}O$— | —$O(CH_2)_6C(CH_3)_3$ |
| 3 | $C_9H_{19}$— | —$O(CH_2)_6C(CH_3)_3$ |
| 4 | $C_8H_{17}O$— | —$O(CH_2)_6OC(CH_3)_3$ |
| 5 | $C_8H_{17}O$— | —$O(CH_2)_6OCH_2$— 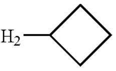 |
| 6 | $C_8H_{17}O$— | —$O(CH_2)_6OCH_2$— 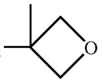 |
| 7 | $C_8H_{17}O$— | —$O(CH_2)_4OCH(CH_3)CH(CH_3)CH_3$ |
| 8 | $C_8H_{17}O$— | —$O(CH_2)_4OCH(CH_3)C(CH_3)_3$ |
| 9 | $C_8H_{17}O$— | —$O(CH_2)_4OCH_2CH(CH_3)CH_3$ |
| 10 | $C_8H_{17}O$— | —$O(CH_2)_4OCH(CH_3)CH_2CH_3$ |
| 11 | $C_8H_{17}O$— | —$O(CH_2)_4OC(CH_3)_2CH_2CH_3$ |
| 12 | $C_8H_{17}O$— | —$O(CH_2)_4OCH_2C(CH_3)_2CH_3$ |
| 13 | $C_9H_{19}$— | —$O(CH_2)_4OCH(CH_3)CH(CH_3)CH_3$ |
| 14 | $C_9H_{19}$— | —$O(CH_2)_4OCH(CH_3)CH_2CH_3$ |
| 15 | $C_9H_{19}$— | —$O(CH_2)_4OC(CH_3)_2CH_2CH_3$ |
| 16 | $C_9H_{19}$— | —$O(CH_2)_4OCH_2C(CH_3)_2CH_3$ |
| 17 | $C_8H_{17}O$— | —$CH_2CH_2CH(CH_3)CH_2C(CH_3)_3$ |
| 18 | $C_8H_{17}O$— | —$CH_2CH_2CH(CH_3)(CH_2)_3CH(CH_3)_2$ |
| 19 | $C_9H_{19}$— | —$CH_2CH_2CH(CH_3)CH_2C(CH_3)_3$ |
| 20 | $C_9H_{19}$— | —$CH_2CH_2CH(CH_3)(CH_2)_3CH(CH_3)_2$ |

Compounds of formula (I) are suitably prepared by using conventional methods. In general they may be prepared by coupling together appropriately substituted ring systems to construct a mesogenic group. For example, they may be prepared by coupling a compound of formula (IV)

$$X—(R_{17}—W_1)_f—Z \quad \text{(IV)}$$

where $R_{17}$, $W_1$ and f are as defined in relation to sub-formula (II), X is as defined in relation to formula (I) and Z is a reactive group such as boronic acid $B(OH)_2$, with a compound of formula (V)

$$L—(R_{18}—W_2)_g—(R_{19})—Y \quad \text{(V)}$$

where Y is defined in relation to formula (I), $R_{18}$, $R_{19}$, $W_2$ and g are as defined in relation to sub-formula (II) and L is a leaving group such as halo, and in particular bromide. The reaction is suitably effected in the presence of a coupling agent such as $Pd(PPh_3)_4$ in an organic solvent such a dimethoxyethane (DME) and in the presence of a base such as an alkali metal carbonate such as $Na_2CO_3$.

Compounds of formula (IV) and (V) are either known compounds or they can be prepared from known compounds by conventional methods. Examples of such methods are illustrated in the examples hereinafter.

Certain compounds of formula (I) are novel and these form a further aspect of the invention. In particular, the invention further provides a compound of formula (VI)

(VI)

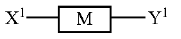

where M is a mesogenic core group, and $X^1$ and $Y^1$ are selected from a functional group, an optionally substituted alkyl chain, an optionally substituted alkenyl chain, an optionally substituted alkynyl chain;

provided that at least one group $X^1$ or $Y^1$ is a group of sub-formula (vi)

(vi)

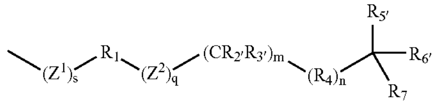

where $Z^1$, $Z^2$, s, q, $R_1$, $R_4$ and $R_7$ are as defined in relation to sub-formula (i), $R_{2'}$, $R_{3'}$, $R_{5'}$ and $R_{6'}$ are independently selected from hydrogen, $C_{1-4}$alkyl, $C_{1-4}$alkoxy;

provided that at least two of the groups $R_{2'}$, $R_{3'}$, $R_{5'}$ and $R_{6'}$ is other than hydrogen.

Preferred variables for M, $Z^1$, $Z^2$, s, q, $R_1$, $R_4$ and $R_7$ in formula (VI) are as defined above in relation to the corresponding variables of formula (I). Similarly preferred examples of groups $X^1$ and $Y^1$ are as defined above in respect of X and Y in formula (I).

Particular examples of groups of sub-formula (vi) are groups of formula (iv) as defined above where at least one of $R_{11}$, $R_{12}$ and $R_{13}$ is other than hydrogen, and in particular are groups of sub-formula (iva), (ivb), (ivc) and (ivd) as defined above.

An alternative group of novel compounds which form a further aspect of the invention are compounds of formula (VII)

(VII)

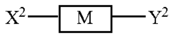

where M is a mesogenic core group, as defined above, and $X^2$ and $Y^2$ are selected from an optionally substituted alkyl chain, an optionally substituted alkenyl chain, an optionally substituted alkynyl chain;

provided that at least one group $X^1$ or $Y^1$ is a group of sub-formula (vii)

(vii)

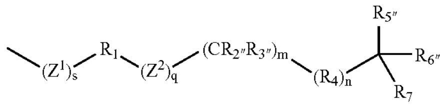

where $Z^1$, $Z^2$, s, q, m, n, $R_1$, $R_4$ and $R_7$ are as defined above in relation to sub-formula (i); at least one of $R_{5''}$ and $R_{6''}$ or $R_{2''}$ and $R_{3''}$ together with the carbon atom to which they are attached form a $C_{3-7}$cycloalkyl or $C_{3-7}$cycloalkoxy group, and the remainder are independently selected from hydrogen, $C_{1-4}$alkyl, $C_{1-4}$alkoxy;

provided that where only one of $X^2$ or $Y^2$ is a group of sub-formula (vii), and the group of formula (vii) is a group of sub-formula (viia)

(viia)

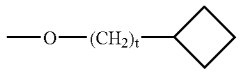

where t is 1-10, then either the group M is other than

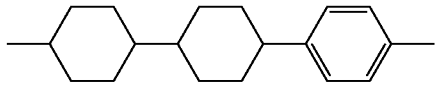

or the other of the group $X^2$ or $Y^2$ is other than alkyl.

A particularly preferred group of compounds of formula (VII) are compounds where the group of sub-formula (vii) is a group of sub-formula (iii) and defined above. and in particular is a group of sub-formula (iiia) and (iiib).

In another preferred embodiment, the invention provides a compound of formula (VII)

(VII)

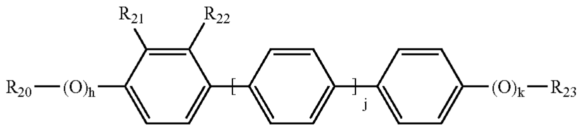

where j, h, and k are independently selected from 0 or 1;

$R_{21}$ and $R_{22}$ are selected from hydrogen or fluorine, and $R_{20}$ and $R_{23}$ are independently selected from alkyl groups having at least 6 carbon atoms and optionally interposed with one or more oxygen or sulphur groups, and at least one of $R_{20}$ or $R_{22}$ has at least one pendent $C_{1-4}$alkyl, $C_{1-4}$alkoxy or a cycloalkyl ring, arranged not more than 6 atoms from the end of the alkyl group.

Compounds of formula (VI), (VII) and (VIII) can be prepared using conventional methods as outlined above for the preparation of compounds of formula I.

The liquid crystal compounds of the invention, in particular the compounds of formula (VI), (VII) or (VIII) may be used alone or in admixture with other liquid crystal compounds which may or may not comprise compounds of formula (I). Such mixtures form a further aspect of the invention.

Compounds of formula (I) have liquid crystal properties and in particular are Smectic C compounds. Thus they may be used in a variety of liquid crystal devices including liquid crystal display cells such as ferroelectric liquid crystal displays, and in particular smectic liquid crystal displays such as surface stabilised ferroelectric liquid crystal (SSFLC) displays.

Such devices which include novel compounds of the invention form a further aspect of the invention.

The invention will now be particularly described by way of example with reference to the accompanying diagrammatic drawings in which.

EXAMPLE 1

Figure 1:
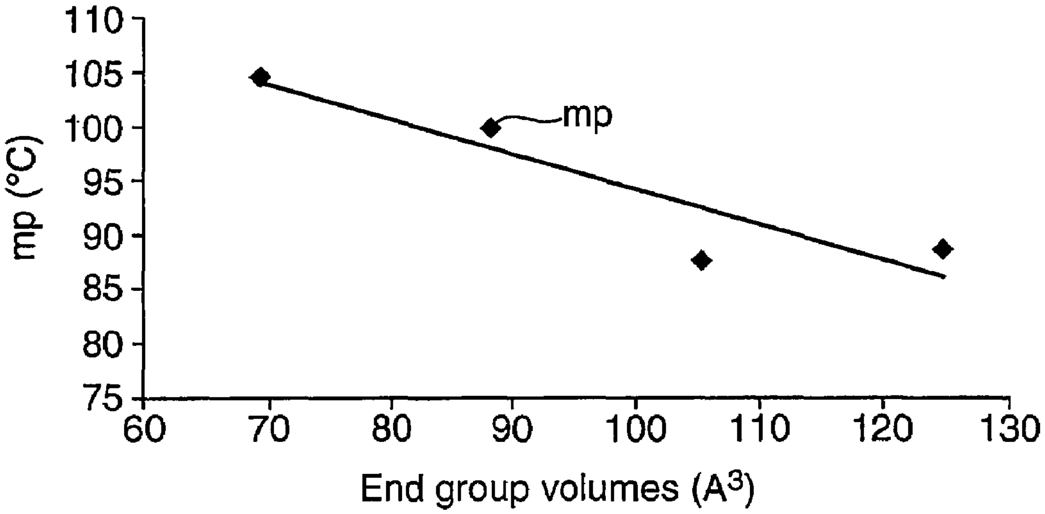
FIG. 1 is a graph showing melting points vs end group volumes for compounds G, 8, 9 and 12 hereinafter.

Preparation of Compound No. 1 in Table 1

This compound was prepared using a combination of Schemes 1 and 2 hereinafter.

Step 1: Preparation of 2,3-Difluorophenylboronic Acid

Butyllithium (2.5 M in hexanes, 88 ml, 0.219 mol) was added dropwise to a stirred, cooled (−78° C.) solution of difluorobenzene (25.0 g, 0.219 mol) in dry THF (400 ml) under a stream of dry nitrogen. The reaction mixture was maintained under these conditions for 2.5 h and then trimethylborate (45.5 g, 0.438 mol) was added dropwise to the reaction mixture and left overnight to reach room temperature. The reaction mixture was stirred for 1 h with 10% HCl (100 ml) at room temperature. The product was extracted into ether (2×200 ml) and the combined ethereal extracts were washed with water and dried ($MgSO_4$), the solvent was removed under reduced pressure to give white crystals.

Yield 31.1 g, 90%; mp 234-237° C.

$^1H$ NMR (270 MHz) δ ($CDCl_3$): 7.10 (1 H, dd, J 7.8), 7.15 (1 H, t, J 7.8), 7.50 (1 H, br s), 7.65 (1 H, t, J 7.8), one proton signal was not detected.

$\nu_{max}$ (KCl): 3700-3000, 1625, 1470, 1360, 1270, 1045, 900 $cm^{-1}$.

m/z: 158 ($M^+$), 140, 125, 114.

Step 2: Preparation of 2,3-Difluorophenol

10% Hydrogen peroxide (160 ml of 100 vol. in 240 ml in water) was added dropwise to a solution of the product of step 1 (31.1 g, 0.202 mol) in ether (100 ml) and heated under reflux overnight. The ether layer was separated and the aqueous layer was washed with ether (100 ml). The combined ethereal layers were washed with 10% sodium hydroxide solution and the separated aqueous layer was acidified with 36% HCl. The product was extracted into ether (2×200 ml), and the combined ethereal layers were washed with brine, water and dried ($MgSO_4$). The solvent was removed in vacuo to give a white solid.

Yield 25.4 g, 99%; mp 35-36° C.

$^1H$ NMR (270 MHz) δ ($CDCl_3$): 5.30 (1 H, s), 6.65-6.80 (2 H, m), 6.90 (1 H, dd, J 7.8).

$\nu_{max}$(KCl): 3700-3000, 1625, 1540, 1515, 1490, 1475, 1350, 1310, 1250, 1190, 1020 $cm^{-1}$.

m/z: 130 ($M^+$), 110 and 101.

Step 3: Preparation of 1,2-Difluoro-3-octyloxybenzene

Potassium carbonate (33.2 g, 0.240 mol) was added to a solution of the product of step 2 (26.0 g, 0.200 mol) in butanone (200 ml). The mixture was left stirring at room temperature and a solution of 1-bromooctane (37.6 g, 0.019 mol) in butanone (50 ml) was added dropwise. The reaction mixture was heated under reflux for 44 h, filtered and the butanone was removed from the filtrate under reduced pressure. The product was extracted into ether (2×150 ml) and the combined ethereal extracts were washed successively with water, 5% sodium hydroxide, water, and dried ($MgSO_4$). The solvent was removed in vacuo and the residue was distilled under reduced pressure to give a colourless oil.

Yield 24.8 g, 53%; bp 164-166° C. at 18 mmHg.

$^1H$ NMR (270 MHz) δ ($CDCl_3$): 0.85 (3 H, t, J 6.2), 1.15-1.35 (8 H, m), 1.45 (2 H, quintet, J 6.2), 1.80 (2 H, quintet, J 6.4), 4.00 (2 H, t, J 6.4), 6.75 (2 H, m), 6.95 (1 H, m).

$\nu_{max}$(KCl): 2950, 2880, 1635, 1525, 1490, 1480, 1325, 1300, 1265, 1090 $cm^{-1}$.

m/z: 242 ($M^+$), 171, 156, 130.

Step 4: Preparation of 2,3-Difluoro-4-octyloxyphenylboronic Acid

Quantities: Product of step 3 (24.0 g, 0.106 mol), butyllithium (2.5 M in hexanes 42.3 ml, 0.106 mol), trimethyl borate (21.9 g, 0.212 mol). The experimental procedure was as described in step 1.

Yield 30.2 g, 100%.

$^1H$ NMR (270 MHz) δ ($CDCl_3$): 0.90 (3 H, t, J 5.9), 1.25-1.35 (8 H, m), 1.45 (2 H, quintet, J 5.9), 1.80 (2 H, quintet, J 6.2), 4.05 (2 H, t, J 6.3), 6.80 (1 H, m), 7.80 (1 H, m), the OH protons were not detected.

$\nu_{max}$(KCl): 3600-3100, 2980, 2940, 2880, 1635, 1530, 1475, 1365, 1310, 1225, 1090 $cm^{-1}$.

m/z: 286 ($M^+$), 271, 258, 241(100%).

Step 5: Preparation of 6-Chlorohexyl toluene-p-sulphonate

A solution of 6-chlorohexan-1-ol (25.0 g, 0.183 mol) in dichloromethane (DCM) (166 ml) and pyridine (33 ml) was cooled to −5° C. Toluene-p-sulphonyl chloride (40.1 g, 0.210 mol) was slowly added to the stirred solution and left to react overnight. The reaction mixture was treated with ice (80 g) and left stirring for 1 h. The organic layer was washed with ice cold 2M-sulphuric acid and then dried ($MgSO_4$). The solvent was removed in vacuo and the residue was purified by column chromatography [DCM] to give a white powder 40.20 g, 85%; mp 27-28° C.

$^1H$ NMR (400 MHz) δ ($CDCl_3$): 1.26-1.44 (4 H, m,), 1.62-1.78 (4 H, m), 2.45 (3 H, s), 3.49 (2 H, t, J 4.8), 4.03 (2 H, t, J 5.0), 7.34 (2 H, d), 7.79 (2 H, d).

$\nu_{max}$(KCl): 2960, 2880, 1610, 1490, 1290, 1260, 820 $cm^{-1}$.

Step 6: Preparation of 1-Chloro-7,7-dimethyloctane

The catalyst used in this reaction was prepared by adding the following reagents to dry THF (12.90 ml), under a stream of dry nitrogen in an ice bath to make a 0.1M solution of catalyst: lithium bromide (0.112 g, 1.29 mmol), lithium thiophenolate (1M in THF 1.29 ml, 1.29 mol) and copper (I) bromide dimethyl sulfide (0.27 g, 1.29 mmol). The catalyst was then added to a solution of the product of step 5 (7.00 g, 0.025 mol) in dry THF (50 ml) the reaction mixture was left to stir for 15 min at room temperature. tert-Butylmagnesium chloride (1M in dry THF, 25.1 ml, 0.025 mol) was added dropwise to the reaction mixture under a stream of dry nitrogen and the reaction mixture was left stirring overnight. The reaction mixture was then washed with DCM and cold water, the chlorinated layer was then dried ($MgSO_4$). The solvent was removed in vacuo and the residue was purified by column chromatography [DCM] to give a colourless oil.

Yield 1.32 g, 30%.

$^1H$ NMR (270 MHz) δ ($CDCl_3$): 0.86 (9 H, s), 1.14-1.18 (2 H, m), 1.20-1.38 (4 H, m), 1.50 (2 H, quintet, J 7.5), 1.81 (2 H, quintet, J 7.1), 3.50 (2 H, t, 7.1).

Step 7: Preparation of 4-Bromo-4'-(7,7-dimethyloctyloxy) biphenyl

Potassium carbonate (0.56 g, 4.8 mmol) was added to a solution of 4-bromo-4'-hydroxybiphenyl (0.80 g, 3.2 mmol) in butanone (50 ml) with potassium iodide (0.1 g) as catalyst. This mixture was left stirring at room temperature for 10 min and a solution of 1-chloro-7,7-dimethyloctance from step 6 (0.50 g, 2.8 mmol) in butanone (10 ml) was added dropwise. The reaction mixture was heated under reflux for 44 h. The mixture was filtered and butanone was removed from the filtrate under reduced pressure. The product was extracted into ether (2×75 ml) and the combined ethereal extracts were washed successively with water, 5% sodium hydroxide and water, and dried ($MgSO_4$). The solvent was removed in vacuo and the residue was purified by column chromatography [DCM] to give a white powder.

Yield 0.80 g, 80%; mp 123-124° C.

$^1H$ NMR (270 MHz) δ($CDCl_3$): 0.86 (9 H, s), 1.14-1.18 (2 H, m,), 1.20-1.38 (4 H, m), 1.50 (2 H, quintet, J 7.5), 1.81 (2 H, quintet, J 7.1), 4.00 (2 H, t, J 7.1), 6.96 (2 H, d), 7.41 (2 H, d), 7.47 (2 H, d), 7.52 (2 H, d).

$\nu_{max}$(KCl): 2960, 2880, 1610, 1490, 1290, 1260, 820 $cm^{-1}$.

m/z: 390/388 ($M^+$), 250/248 (100%), 141, 57.

Step 8: Preparation of 4"-(7,7-Dimethyloctyloxy)-2,3-difluoro-4-octyloxyterphenyl The product of step 7 (0.40 g, 1.1 mmol) and a 2M-aqueous solution of sodium carbonate (40 ml) and tetrakis(triphenylphosphine)palladium(0) (0.06 g, 0.06 mmol) were mixed in DME (60 ml) under dry nitrogen at room temperature to which 2,3-difluoro-4-octyloxyphenylboronic acid from step 4 (0.37 g, 1.3 mmol) was added. The stirred reaction mixture was heated under reflux under dry nitrogen overnight until g.l.c. and t.l.c. revealed a complete reaction. The product was extracted into DCM (2×50 ml) and washed with brine, water and dried ($MgSO_4$). The solvent was removed under reduced pressure and the residue was purified by column chromatography [DCM-hexane, 1:5] and recrystallised from hexane and a trace of ethanol to give white crystals of compound 1 in Table 1.

Yield 0.42 g, 70%.

Transition temperatures (° C.): Cr 97.3 SmC 160.1 I.

$^1H$ NMR (400 MHz) δ ($CDCl_3$): 0.86-0.92 (12 H, m), 1.15-1.21 (2 H, m,), 1.29-1.37 (12 H, m), 1.44-1.52 (4 H, m), 1.76-1.89 (4 H, m), 3.99 (2 H, t, J 6.4), 4.08 (2 H, t, J 6.6), 6.78-6.84 (1 H, m), 6.99 (2 H, d), 7.10-7.16 (1 H, m), 7.54-7.57 (2×2 H, d), 7.62 (2 H, d).

$\nu_{max}$(KCl): 2960, 2880, 1500, 1400, 1290, 1260, 1080, 800 $cm^{-1}$.

m/z: 550 ($M^+$), 438 (100%), 410, 298, 57.

EXAMPLE 2

Preparation of Compound No. 2 in Table 1

Step 1: Preparation of 4-Bromo-4'-(3,7-dimethyloctyloxy) biphenyl

4-Bromo-4'-hydroxybiphenyl (2.50 g, 0.010 mol) and 3,7-dimethylactan-1-ol (1.58 g, 0.010 mol) were mixed in dry tetrahydrofuran (THF) (50 ml) and left stirring at room temperature for 10 min; then a solution of triphenylphosphine (2.60 g, 0.010 mol) and diethylazodicarboxylate (DEAD) (1.75 g, 0.010 mol) in dry cold THF (50 ml) was added dropwise at room temperature over 10 min. The reaction mixture was left stirring overnight. The reaction product was extracted in ether (2×100 ml), and the combined ethereal solutions were washed with water and dried ($MgSO_4$). The crude product was adsorbed onto silica gel and purified by column chromatography [ethyl acetate-petroleum fraction (bp 40-60° C.), 1:5] to give a white powder.

Yield 2.92 g, 75%; mp 101-102° C.

$^1H$ NMR (270 MHz) δ ($CDCl_3$): 0.85 (6 H, d, J 6.5), 0.95 (3 H, d, J 6.3), 1.12-1.40 (6 H, m), 1.47-1.74 (3 H, m), 1.78-1.89 (1 H, m), 4.02 (2 H, t, J 5.9), 6.96 (2 H, d), 7.37-7.54 (3×2H, d).

$\nu_{max}$(KCl): 2940, 1610, 1460, 1290, 1190, 820, 500 $cm^{-1}$.

m/z: 394/392 ($M+4^+$), 250/248, 152, 101, 89 (100%).

Step 2: Preparation of 4"-(3,7-Dimethyloctyloxy)-2,3-difluoro-4-octyloxyterphenyl (Compound 2)

4-Bromo-4'-(3,7-dimethyloctyloxy)biphenyl (0.80 g, 2.0 mmol) from step 1, an aqueous solution 2M-sodium carbonate (40 ml) and tetrakis(triphenylphosphine)palladium(0) (0.12 g, 0.12 mmol) were mixed in DME (60 ml) under dry nitrogen at room temperature and 2,3-difluoro-4-octyloxyphenylboronic acid (0.62 g, 2.2 mmol), prepared as described in Example 1 step 4, was added. The stirred reaction mixture was heated overnight under reflux under dry nitrogen until g.l.c. and t.l.c. revealed a complete reaction. The product was extracted into DCM (2×150 ml) and washed with brine, water and dried ($MgSO_4$). The solvent was removed under reduced pressure and the residue was purified by column chromatography [ether-hexane, 3:1] and recrystallised from ethanol to give the desired compound as white crystals.

Yield 0.78 g, 65%.

Transition temperatures (° C.): Cr 82.5 SmC 132.2 N 138.0 I.

$^1H$ NMR (270 MHz) δ ($CDCl_3$): 0.84-0.92 (9 H, m), 0.96 (3 H, d, J 6.0), 1.10-1.42 (18 H, m), 1.44-1.65 (4 H, m), 3.82 (2 H, t, J 5.4), 4.02 (2 H, t, J 5.8), 6.78-6.85 (1 H, m), 7.00 (2 H, d), 7.10-7.16 (1 H, m), 7.52-7.66 (3×2 H, d).

$\nu_{max}$(KCl): 2980, 2880, 1610, 1505, 1480, 1305, 1260, 1200, 1080, 800 $cm^{-1}$.

m/z: 550 ($M^+$) (100%), 423, 393, 298, 57.

EXAMPLE 3

Preparation of Compound No. 3 in Table 1

Step 1: Preparation of (2,3-Difluorophenyl)nonan-1-ol

Butyllithium (2.5 M in hexanes 52.5 ml, 0.131 mol) was added dropwise to a stirred, cooled (−78° C.) solution of difluorobenzene (12.0 g, 0.105 mol) in dry THF (400 ml) under a stream of dry nitrogen. The reaction mixture was maintained under these conditions for 2.5 h and a solution of nonanal (14.9 g, 0.105 mol) in dry THF (50 ml) was added dropwise at −78° C. The mixture was allowed to slowly reach room temperature overnight. Ammonium chloride solution (2M, 200 ml) was added and the product was extracted into ether (2×150 ml), the combined ethereal extracts were washed with water and dried ($MgSO_4$). The solvent was removed in vacuo and the residue was distilled under reduced pressure to give a colourless oil.

Yield 19.5 g, 70%; bp 120-126° C. at 0.1 mmHg.

$^1H$ NMR (270 MHz) δ ($CDCl_3$): 0.85 (3 H, t, J 5.7), 1.15-1.40 (12 H, m), 1.70-1.80 (2 H, m), 2.95 (1 H, s), 5.00 (1 H, t, J 6.2),7.00-7.10 (2 H, m), 7.12-7.20 (1 H, m).

$\nu_{max}$(KCl): 3600-3100, 2940, 2860, 1630, 1600, 1485, 1270, 1210, 1060, 820 $cm^{-1}$.

m/z: 256 ($M^+$), 238, 216, 203.

Step 2: Preparation of 1,2-Difluoro-3-nonylbenzene

Phosphorous pentoxide (34.1 g, 0.240 mol) was added to a stirred solution of the product of step 1 (19.5 g, 0.095 mol) in pentane (150 ml). The mixture was stirred at room temperature overnight and the mixture was filtered. 5% Palladium-on-charcoal (1.85 g) was added to the filtrate and the stirred mixture was hydrogenated at room temperature overnight. The mixture was filtered and pentane was removed in vacuo and the product was distilled to give a colourless oil.

Yield 12.1 g, 65%; bp 150-156° C. at 15 mmHg.

$^1$H NMR (270 MHz) δ ($CDCl_3$): 0.90 (3 H, t, J 6.1), 1.50-1.65 (12 H, m), 1.68 (2 H, quintet, J 6.3), 1.72 (2 H, t, J 6.3), 6.91-7.01 (3 H, m).

$\nu_{max}$(KCl): 2980, 2960, 2860, 1630, 1600, 1490, 1285, 1210, 1040, 995, 825, 780, 730 $cm^{-1}$.

m/z: 240 ($M^+$), 197, 182.

Step 3: Preparation of 2,3-Difluoro-4-nonylphenylboronic Acid

Butyllithium (2.5 M in hexanes, 20.0 ml, 0.050 mol) was added dropwise to a stirred, cooled (−78° C.) solution of the product of step 2 (12.0 g, 0.050 mol) in dry THF (250 ml) under a stream of dry nitrogen. The reaction mixture was maintained under these conditions for 2.5 h and then trimethyl borate (10.4 g, 0.100 mol) was added dropwise and the reaction mixture was left overnight to reach room temperature.

The reaction mixture was stirred for 1 h with 10% HCl (100 ml) at room temperature. The product was extracted into ether (2×200 ml) and the combined ethereal extracts were washed with water and dried ($MgSO_4$); the solvent was removed under reduced pressure to give white crystals.

Yield 14.2 g, 95% (mp not recorded).

$^1$H NMR (270MHz) δ ($CDCl_3$): 0.90 (3 H, t, J 5.7), 1.25-1.35 (12 H, m), 1.60 (2 H, m), 2.67 (2 H, t, J 6.3), 7.00-7.05 (1 H, m), 7.35-7.42 (1 H, m), the OH protons were not detected.

$\nu_{max}$(KCl): 3600-3100, 2960, 2940, 2850, 1640, 1460, 1435, 1250, 1220, 1135, 670 $cm^{-1}$.

m/z: 267, 256, 213, 199, 184.

Step 4: Preparation of 4"-(7,7-Dimethyloctyloxy)-2,3-difluoro-4-nonylterphenyl (Compound 3)

Quantities: compound 1, prepared as described in Example 1, (0.40 g, 1.1 mmol), tetrakis(triphenylphosphine)-palladium(0) (0.06 g, 0.06 mmol), 2,3-Difluoro-4-nonylphenylboronic acid (0.37 g, 1.3 mmol) prepared as described in step 3. The reaction procedure was as described for the preparation of compound 1 in step 8 of Example 1.

Yield 0.39 g, 65% (white powder).

Transition temperatures (° C.): Cr 60.4 SmC 126.5 I.

$^1$H NMR (400 MHz) δ ($CDCl_3$): 0.87 (9 H, s), 0.89 (3 H, t, J 6.3), 1.15-1.37 (18 H, m,) 1.50 (2 H, quintet, J 7.6), 1.65 (2 H, quintet, J 7.4), 1.82 (2 H, quintet, J 6.9), 2.69 (2 H, t, 7.4), 4.00 (2 H, t, J 6.3), 6.98-7.02 (3 H, m), 7.12-7.16 (1 H, m), 7.57-7.65 (3×2 H, d).

$\nu_{max}$(KCl): 2880, 2865, 1460, 1250, 820 $cm^{-1}$.

m/z: 548 ($M^+$), 536, 408 (100%), 295, 73.

EXAMPLE 4

Preparation of Compound No. 4 in Table 1

Step 1: Preparation of 6-Bromohexan-1-ol

Hydrobromic acid (48.5%, 36 ml, 0.221 mol), was added to a solution of hexan-1,6-diol (25.0 g, 0.221 mol) in benzene (200 ml). The mixture was heated under reflux for 26 h and the water formed was removed using a Dean-Stark water separator. Benzene was removed in vacuo, the residue was dissolved in diethyl ether (300 ml), washed with 6N sodium hydroxide solution (250 ml) and water (250 ml). The etheral solution was then dried ($MgSO_4$) and the solvent was removed in vacuo; the residue was purified by column chromatography [DCM] to give a colourless oil.

Yield 19.9 g, 50%; bp 108-110° C. at 5 mmHg.

$^1$H NMR (270 MH) δ ($CDCl_3$): 1.35-1.52 (4 H, m), 1.60 (2 H, quintet, J 5.8), 1.80 (2 H, quintet, J 6.0), 3.42 (2 H, t, J 5.8), 3.70 (2 H, t, J 6.0) the OH proton was not detected.

$\nu_{max}$(KCl): 3600, 2900, 2800, 1440, 1280, 1250, 720, 500 $cm^{-1}$.

m/z: 182/180 ($M^+$), 102/100 (100%).

Step 2: Preparation of 4-Bromo-4'-(6-hydroxyhexyloxy)biphenyl

A solution of 6-bromohexan-1-ol (3.64 g, 0.020 mol) from step 1 in butanone (80 ml) was added at room temperature to a stirred mixture of 4-bromo-4-'-hydroxybiphenyl (5.00 g, 0.020 mol) and potassium carbonate (5.50 g, 0.040 mol) in butanone (70 ml). The reaction mixture was heated under reflux for 48 h. The potassium carbonate was filtered off and the solvent was removed in vacuo, the residue was dissolved in diethyl ether (250 ml) and washed with water (2×150 ml) and dried ($MgSO_4$). The solvent was removed in vacuo and the crude solid was then recrystallised from ethanol to give white crystals.

Yield 3.60 g, 49%; mp 140-141° C.

$^1$H NMR (270 MHz) δ ($CDCl_3$): 1.36-1.64 (6 H, m), 1.81 (2 H, quintet, J 5.8), 2.81 (1 H, s), 3.52 (2 H, t, J 5.0), 4.00 (2 H, t, J 6.0), 6.95 (2 H, d), 7.38-7.56 (3×2 H, d).

$\nu_{max}$(KCl): 3360, 2980, 2890, 1610, 1480, 1390, 1260, 1080, 1005, 810, 500 $cm^{-1}$.

m/z: 350/348 ($M^+$), 250/248 (100%), 244, 218, 192, 138, 114, 58 (100%).

Step 3: Preparation of 2,3-Difluoro-4-octyloxy-4"-(6-hydroxyhexyloxy)terphenyl

A solution of 4-bromo-4'-(6-hydroxyhexyloxy)biphenyl (3.30 g, 9.5 mmol) from step 2, a 2M-aqueous solution of sodium carbonate (40 ml) and tetrakis(triphenylphosphine) palladium(0) (0.28 g, 0.28 mmol) were mixed in DME (60 ml) under dry nitrogen at room temperature and 2,3-difluoro-octyloxyphenylboronic acid (3.25 g, 11.4 mmol) prepared as described in Example 1 step 4, was added. The stirred reaction mixture was heated under reflux under dry nitrogen overnight until g.l.c. and t.l.c. revealed a complete reaction. The product was extracted into DCM (2×150 ml) and washed with brine, water and dried ($MgSO_4$). The solvent was removed under reduced pressure and the residue was purified by column chromatography [DCM-hexane, 1:1] and recrystallised from ethanol-hexane (1:4) to give a white powder.

Yield 1.20 g, 30%.

Transition temperatures (° C.): Cr 158.3 SmC 168.9 SmA 179.5 N 185.0 I.

$^1$H NMR (270 MHz) δ ($CDCl_3$): 0.90 (3 H, t, J 6.3), 1.24 (1 H, s), 1.22-1.40 (16 H, m), 1.80-1.88 (4 H, m), 3.67 (2 H, t, J 6.1), 4.02 (2 H, t, J 5.9), 4.08 (2 H, t, J 6.1), 6.78-6.83 (1 H, m), 6.88 (2 H, d), 7.08-7.13 (1 H, m), 7.52-7.58 (2×2 H, d), 7.67 (2 H, d).

$\nu_{max}$(KCl): 3600-3300, 2930, 2850, 1600, 1495, 1390, 1300, 1250, 1070, 800 $cm^{-1}$.

m/z: 510 ($M^+$), 493, 298, 87 (100%).

Step 4: Preparation of 4"-(9,9-Dimethyl-1,8dioxadecyl)-2,3-difluoro-4-octyloxyterphenyl (Compound No. 4)

A solution of the product from step 3 (1.10 g, 2.1 mmol) in a minimum volume of DCM (100 ml of hexane was added to reduce the polarity of the solvent) was prepared and t-butyl trichloroacetimidate (0.91 g, 4.2 mmol), and a catalytic amount of boron trifluoride etherate (20 μl) were added at room temperature. The reaction mixture was left stirring until g.l.c. and t.l.c. analyses revealed a complete reaction. The solvent was removed in vacuo and the product was purified by column chromatography [DCM] and recrystallised from ethanol to give a white powder.

Yield 0.80 g, 67%.

Transition temperatures (° C.): Cr 99.1 $SmC_{alt}$ 119.8 SmC 151.8 I.

$^1$H NMR (270 MHz) δ ($CDCl_3$): 0.85-0.97 (3 H, m), 1.20 (9 H, s), 1.24-1.26 (16 H, m), 1.77-1.90 (4 H, m), 3.35 (2 H, t, J 5.6), 4.01 (2 H, t, J 5.5), 4.08 (2 H, t, 5.3), 6.78-6.85 (1 H, m), 7.00 (2 H, d), 7.10-7.16 (1 H, m), 7.52-7.66 (3×2 H, d).

$\nu_{max}$(KCl): 2980, 1640, 1500, 1480, 1300, 1080, 800 $cm^{-1}$.

m/z: 566 ($M^+$), 423, 298, 83, 57.

EXAMPLE 5

Preparation of Compound No. 5 in Table 1

Step 1: Preparation of 6-(4'-Bromobiphenyl)hexyl toluene-p-sulphonate

A solution of 4-bromo-4'-(6-hydroxyhexyloxy)biphenyl (5.00 g, 0.0143 mol) prepared as described in Example 4 step 2 in DCM (166 ml) and pyridine (33 ml) was cooled to −5° C. Toluene-p-sulphonylchloride (3.00 g, 0.0160 mol) was slowly added to the stirred solution which was left to react overnight. The reaction mixture was treated with ice (10 g) and left string for 1 h. The reaction mixture was washed with ice cold sulphuric acid and water and the organic layer was then dried ($MgSO_4$). The solvent was removed in vacuo and the residue was purified by column chromatography [DCM] to give a white powder.

Yield 5.70 g, 80%.

$^1$H NMR (400 MHz) δ ($CDCl_3$): 1.35-1.48 (4 H; m), 1.68 (2 H, quintet, J 6.2), 1.75 (2 H, quintet, J 5.8), 2.44 (3 H, s), 3.95 (2 H, t, J 6.2), 4.04 (2 H, t, J 5.8), 6.93 (2 H, d), 7.33 (2 H, d), 7.40 (2 H, d), 7.48 (2 H, d), 7.52 (2 H, d), 7.79 (2 H, d).

$\nu_{max}$(KCl): 2980, 1605, 1490, 1300, 1260, 1080, 1000, 1060, 820, 680 $cm^{-1}$.

Step 3: Preparation of 4-Bromo-4'-[6-(cyclobutylmethoxy) hexyloxy]biphenyl

A solution of (4'-Bromobiphenyl-4-yl)hexyl toluene-p-sulphonate (2.50 g, 5.0 mmol) from step 2 in DMSO (50 ml) was cooled to −5° C. and potassium hydroxide powder (Fluka, 1.03 g, 0.018 mol) was added and the mixture was stirred using a mechanical stirrer, a solution of cyclobutylmethanol (0.80 g, 10.0 mmol) in DMSO (15 ml) was added dropwise. The reaction mixture was kept at −5° C. for 1 h and then removed from the cooling bath for a further 2 h. The product was extracted in hexane (150 ml) and washed with water in order to remove all traces of DMSO. Hexane was removed under reduced pressure and the residue was purified by column chromatography [DCM-hexane, 1:6] to give a white powder.

Yield 1.55 g, 75%; mp 101-102° C.

$^1$H NMR (400 MHz) δ ($CDCl_3$): 1.37-1.96 (8 H, m), 2.00-2.11 (5 H, m), 2.56 (2 H, m), 3.29 (2 H, d, J 7.6), 3.42 (2 H, t, J 7.6), 4.00 (2 H, t, J 5.7), 6.95 (2 H, d), 7.40 (2 H, d), 7.46 (2 H, d), 7.52 (2 H, d).

$\nu_{max}$(KCl): 2980, 2880, 1605, 1490, 820 $cm^{-1}$.

m/z: 418/416 ($M^+$), 348, 337, 250/248, 169.

Step 4: Preparation of 4"-[6-(Cyclobutylmethoxy)hexyloxy]-2,3-difluoro-4-octyloxyterphenyl (Compound 5)

4-Bromo-4'-[6-(cyclobutylmethoxy)hexyloxy]biphenyl (0.70 g, 1.7 mmol) from step 3 and a 2M-aqueous solution of sodium carbonate (40 ml) were mixed in DME (60 ml) and with tetrakis(triphenylphosphine)-palladium(0) (0.12 g, 0.12 mmol) under dry nitrogen; to which 2,3-difluoro-4-octyloxyphenylboronic acid (prepared as described in Example 1 step 4) (0.58 g, 2.0 mmol) was added. The stirred reaction mixture was heated under reflux overnight. The product was extracted into DCM and washed with brine, water and dried ($MgSO_4$). The solvent was removed under reduced pressure and the residue was purified by column chromatography [DCM-hexane, 1:5] and recrystallised from hexane to give white crystals.

Yield 0.70 g, 72%.

Transition temperatures (° C.): Cr 92.5 SmC 148.1 I.

$^1$H NMR (400 MHz) δ ($CDCl_3$): 0.88 (3 H, t, J 7.1), 1.22-1.52 (14 H, m), 1.57 (2 H, quintet, J 7.1), 1.68-1.91 (8 H, m), 1.96-2.05 (2 H, m), 2.51 (1 H, ht, J 7.3), 3.36 (2 H, d, J 7.3), 3.38 (2 H, t, J 6.8), 4.00 (2 H, t, J 6.2), 4.07 (2 H, t, J 6.2), 6.81-6.86 (1 H, m), 6.96 (2 H, d, J 8.3), 7.13-7.18 (1 H, m), 7.53-7.57 (4 H, m), 7.61-7.64 (2 H, m).

$\nu_{max}$(KCl): 2980, 2880, 1500, 1470, 1310, 1260, 1120, 1080, 800 $cm^{-1}$.

m/z: 578($M^+$), 482, 370, 298, 101 (100%).

EXAMPLE 6

Preparation of Compound No 6 in Table 1

Step 1: Preparation of 4-Bromo-4'-(6-bromohexyloxy)biphenyl

A solution of triphenylphosphine (3.46 g, 0.013 mol) and DEAD (2.30 g, 0.012 mol) in dry cold THF (100 ml) was added dropwise over 10 min to a solution of 4-bromo-4'-hydroxybiphenyl (3.00 g, 0.012 mol) and 4-bromo-4'-(6-hydroxyhexyloxy)biphenyl (2.20 g, 0.012 mol) (prepared as described in Example 4 step 2 above) in dry THF (50 ml) stirring at room temperature. The reaction mixture was left stirring overnight The reaction product was extracted into diethyl ether (2×200 ml), and the combined ethereal solutions were washed with water and dried ($MgSO_4$). The crude product was adsorbed onto silica gel and purified by column chromatography [DCM-petroleum fraction (bp 40-60° C.), 1:6] and recrystallised from ethanol to give white crystals.

Yield 3.25 g, 60%; mp 109-110° C.

$^1$H NMR (270 MHz) δ ($CDCl_3$): 1.47-1.62 (4 H, m), 1.75-2.00 (4 H, m), 3.43 (2 H, t, J 6.3), 4.00 (2 H, t, J 5.9), 6.87-7.01 (2 H, d), 7.37-7.57 (3×2 H, d).

$\nu_{max}$(KCl): 2980, 1605, 1480, 1000, 810 $cm^{-1}$.

m/z: 414/412/410 ($M^{30}$), 334/332/330, 250/248, 57 (100%).

Step 2: Preparation of 4"-(6-Bromohexyloxy)-2,3-difluoro-4-octyloxyterphenyl

4-Bromo-4'-(6-bromohexyloxy)biphenyl (1.02 g, 2.5 mmol) from step 1 and a 2M-aqueous solution of sodium carbonate (40 ml) were mixed in DME (60 ml) with tetrakis (triphenylphosphine)palladium(0) (0.12 g, 0.12 mmol) under dry nitrogen and compound 5 (0.85 g, 3.0 mmol) was added. The stirred reaction mixture was heated under reflux overnight. The product was extracted into DCM (100 ml) and washed with brine and water and dried ($MgSO_4$). The solvent was removed under reduced pressure and the residue was purified by column chromatography [DCM-hexane, 1:5] and recrystallised from hexane to give a white powder.

Yield 0.80 g, 70%.

Transition temperatures (° C.): Cr 100.7 SmA 117.8 I.

$^1$H NMR (40.0 MHz) δ ($CDCl_3$): 0.89 (3 H, t, J 6.8), 1.23-1.42 (8 H, m), 1.44-1.60 (6 H, m), 1.78-1.94(6 H, m), 3.44 (2 H, t, J 6.8), 4.02 (2 H, t, J 6.7), 4.09 (2 H, t, J 6.7), 6.78-6.84 (1 H, m), 6.98 (2 H, d), 7.10-7.16 (1 H, m), 7.54-7.57 (2×2 H, d), 7.63 (2 H, d).

$\nu_{max}$(KCl): 2970, 2880, 1500, 1470, 1310, 1260, 1080, 800 $cm^{-1}$.

m/z: 574/572 ($M^+$), 460, 298, 269, 71.

Step 3: Preparation of 2,3-Difluoro-4"-[6-(3-methyloxetan-3-ylmethoxy)hexyloxy]-4-octyloxyterphenyl (Compound 6)

A solution of the product from step 2 (0.70 g, 1.7 mmol) in diethyl ether (50 ml) was cooled to 0° C. in an ice bath with a sodium hydroxide aqueous solution (50 ml of solution prepared by mixing 50 g of sodium hydroxide and 100 ml of water) and t-butylammonium bromide (0.10 g used as phase transfer catalyst), to which a solution of 3-(hydroxymethyl)-3-methyloxetane (0.50 g, 5.0 mmol) in hexane (70 ml) was added dropwise over 1 h with vigorous mechanical stirring. The reaction mixture was allowed to warm to room temperature and left stirring for 2 h, then the reaction mixture was heated under reflux for 4 h. The organic layer was collected, dried ($MgSO_4$) and the solvent was removed in vacuo. The crude oil was purified by column chromatography [DCM-petroleum fraction (bp 40-60° C.), 1:5] to give a white powder.

Yield 0.66 g, 66%.

Transition temperatures (° C.): Cr 97.7 SmC 124.8 N 137.8 I.

$^1$H NMR (400 MHz) δ ($CDCl_3$): 0.93 (3 H, t, J 6.8), 1.22-1.42 (13 H, m), 1.43-1.57 (6 H, m), 1.77-1.90 (4 H, m), 3.47-3.53 (4 H, m), 4.02 (2 H, t, J 7.3), 4.08 (2 H, t, J 7.3), 4.30 (2 H, t, J 6.2), 4.52 (2 H, t, J 6.2), 6.77-6.85 (1 H, m), 6.97 (2 H, d), 7.10-7.16 (1 H, m), 7.52-7.59 (2×2 H, d), 7.63 (2 H, d).

$\nu_{max}$(KCl): 2932, 2854, 1635, 1606, 1500, 1469, 1080, 800 $cm^{-1}$.

m/z: 594 ($M^+$), 410, 297, 269, 55.

EXAMPLE 7

Preparation of Compound 7 in Table 1

Step 1: Preparation of 1-Bromo-4-(1,2-dimethylpropyloxy) butane

A solution of 1,4-dibromo-n-butane (119.20 g, 0.0903 mol) in hexane (80 ml) was cooled at 0° C. with a sodium hydroxide aqueous solution (150 ml of solution prepared by mixing 75 g of sodium hydroxide and 150 ml of water) and tert-butylammonium bromide (4.4 mol %, 0.68 g, used as phase transfer catalyst), and a solution of 1,2-dimethylpropan-1-ol (1.27 g, 0.022 mol) in hexane (70 ml) was added dropwise over 1 h with vigorous mechanical stirring. The reaction mixture was allowed to warm to room temperature and left stirring for 2 h, the reaction mixture was then heated under reflux for 4 h. The organic layer was collected and dried ($MgSO_4$) and the solvent was removed in vacuo. The crude oil was purified by column chromatography [DCM-petroleum fraction (bp 40-60° C.), 1:51] to give a colourless oil.

Yield 4.46 g 451%.

$^1$H NMR (270 MHz) δ ($CDCl_3$): 0.86 (3 H, d, J 7.3), 0.89 (3 H, d, J 7.3), 1.06 (3 H, d, J 6.4), 1.60-1.75 (2 H, m), 1.95-2.00 (3 H, m), 3.10 (1 H, quintet, J 6.4), 3.31-3.37 (1 H, m), 3.45 (2 H, t, J 6.4), 3.49-3.55 (1 H, m).

$\nu_{max}$(KCl): 2980, 2880, 1480, 1460, 1380, 1260, 1110 $cm^{-1}$.

m/z: 137, 71, 67, 56 (100%).

Step 2: Preparation of 4-Bromo-4'-(4-(1,2-dimethylpropyloxy)butyloxy)biphenyl

A solution of 4-bromo-4'-hydroxybiphenyl (1.34 g, 5.4 mmol) in butanone (80 ml) was added at room temperature to a stirring mixture of the product of step 1 (1.20 g, 0.010 mol) and potassium carbonate (2.24 g, 0.023 mol) in butanone (70 ml) and the reaction mixture was heated under reflux for 48 h. Potassium carbonate was filtered off and the solvent was removed in vacuo, the residue was dissolved in diethyl ether (250 ml) and washed with water (2×150 ml) and dried ($MgSO_4$). The solvent was removed in vacuo and the residue was purified by column chromatography [DCM-hexane, 1:8] and recrystallised from ethanol to give a white crystals.

Yield 1.25 g, 60%; mp 115-116° C. (white crystals).

$^1$H NMR (400 MHz) δ ($CDCl_3$): 0.87 (6 H, d, J 6.5), 0.91 (3 H, d, J 6.5), 1.66-1.81 (3 H, m), 1.82-1.97 (2 H, m), 3.12 (1 H, q, J 4.6), 3.34-3.45 (1 H, m), 3.52-3.63 (1 H, m), 4.05 (2 H, t, J 6.4), 6.95 (2 H, d), 7.40 (2 H, d), 7.52 (2 H, d) 7.60 (2 H, d).

$\nu_{max}$(KCl): 2990, 2880, 1610, 1490, 1295, 1260, 1120, 1060, 820, 500 $cm^{-1}$.

m/z: 392/390 ($M^+$), 305, 263, 250/248 (100%), 152, 139.

Step 3: Preparation of 4"-[4-(1,2-Dimethylpropyloxy)butyloxy)]-2,3-difluoro-4-octyloxyterphenyl (Compound 7)

The product from step 2 (0.70 g, 1.8 mmol), and a 2M-aqueous solution of sodium carbonate (40 ml), were mixed in tert-butyl methyl ether (TBME) (60 ml), and tetrakis (triphenylphosphine)palladium(0) (0.12 g, 0.12 mmol) under dry nitrogen and 2,3-difluoro-4-octyloxyphenyboronic acid, prepared as described in Example 1 step 4, (0.62 g, 2.1 mmol) were added to the reaction mixture. The stirred reaction mixture was heated under reflux overnight. The product was extracted into DCM (100 ml) and washed with brine, water and dried ($MgSO_4$). The solvent was removed under reduced pressure and the residue was purified by column chromatography [DCM-hexane, 1:5] and recrystallised from hexane to give white powder.

Yield 0.52 g, 55% (white powder).

Transition temperatures (° C.): Cr 84.5 SmC 142.8 I.

$^1$H NMR (400 MHz) δ ($CDCl_3$): 0.84-0.94 (9 H, m), 1.08 (3 H, m), 1.22-1.50 (15 H, m), 1.65-1.96 (2 H, m), 3.14 (1 H, q, J 5.8), 3.36-3.46 (1 H, m), 3.56-3.66 (1 H, m), 4.04 (2 H, t, J 6.4), 4.08 (2 H, t, J 6.4), 6.78-6.86 (1 H, m), 6.98 (2 H, d), 7.08-7.18 (1 H, m), 7.52-7.66 (3×2 H, d).

$\nu_{max}$(KCl): 2980, 2960, 2880, 1500, 1480, 1310, 1260, 1120, 1080, 800 $cm^{-1}$.

m/z: 552 ($M^+$), 465, 410, 352, 298 (100%), 280, 251, 176, 143, 115, 73 (100%).

EXAMPLE 8

Preparation of Compounds 8-16 in Table 1

Using a method analogous to that described in Example 7 but with the appropriate starting alcohol and boronic acid, the following compounds were prepared:

Compound 8 in Table 1:—2,3-Difluoro-4-octyloxy-4"-[4-(1,2,2-trimethylpropyloxybutyloxy]terphenyl Yield 0.55 g, 65% (white powder).

Transition temperatures (° C.): Cr 88.7 SmC 139.4 I.

$^1$H NMR (400 MHz) δ ($CDCl_3$): 0.85-0.95 (12 H, m), 1.05 (3 H, d, J 6.7), 1.24-1.42 (6 H, m), 1.44-1.53 (4 H, m), 1.73 (2 H, quintet, J 6.9), 1.80-1.97 (4 H, m), 2.98 (1 H, q, J 6.1), 3.32 (1 H, dt, J 6.3), 3.64 (1 H, dt, J 6.3), 4.04 (2 H, t, J 6.7), 4.08 (2 H, t, J 6.7), 6.78-6.84 (1 H, m), 6.98 (2 H, d), 7.10-7.16 (1 H, m), 7.51-7.57 (2×2 H, d), 7.63 (2 H, d).

$\nu_{max}$(KCl): 2980, 2960, 2880, 1500, 1470, 1500, 1260, 1115, 1080, 820, 800 $cm^{-1}$.

m/z: 566 ($M^+$), 465, 409, 298 (100%), 157.

Compound 9 in Table 1: 2,3-Difluoro-4"-[4-(1-methylpropyloxy)butyloxy]-4-octyloxyterphenyl Yield 0.49 g, 57% (white powder).

Transition temperatures (° C.): Cr 99.7 SmC 155.5 I.

$^1$H NMR (400 MHz) δ ($CDCl_3$): 0.87-0.94 (6 H, m), 1.13 (3 H, d, J 6.1), 1.29-1.35 (8 H, m), 1.40-1.60 (4 H, m), 1.75 (2 H, quintet, J 6.1), 1.81-1.93 (4 H, m), 3.31 (1 H, sextet, J 6.1), 3.46 (1 H, dt, J 6.1), 3.56 (1 H, dt, J 6.1), 4.04 (2 H, t, J 6.5), 4.08 (2 H, t, J 6.5), 6.78-6.83 (1 H, m), 6.98 (2 H, d), 7.10-7.16 (1 H, m), 7.54-7.57 (2×2 H, d), 7.64 (2 H, d).

$\nu_{max}$(KCl): 2980, 2880, 1610, 1500, 1480, 1310, 1260, 1080, 810, 800 $cm^{-1}$.

m/z: 538 ($M^+$), 465, 439, 409, 143 (100%).

Compound 10 in Table 1: 2,3-Difluoro-4"-[4-(2-methylpropyloxy)butyloxy]-4-octyloxyterphenyl Yield 0.55 g, 65% (white powder).

Transition temperatures (° C.): Cr 92.0 SmC 148.7 I.

$^1$H NMR (400 MHz) δ ($CDCl_3$): 0.88 (3 H, d, J 7.3), 0.91 (6 H, d, J 6.4), 1.30-1.54 (10 H, m), 1.73-1.94 (7 H, m), 3.20 (2 H, d, J 6.8), 3.49 (2 H, t, J 6.2 ), 4.04 (2 H, t, J 6.9), 4.08 (2 H, t, J 6.6), 6.78-6.83 (1 H, m), 6.98 (2 H, d), 7.11-7.16 (1 H, m), 7.52-7.58 (2×2 H, d), 7.63(2 H, d).

$\nu_{max}$(KCl): 2980, 2940, 2880, 1500, 1470, 1300, 1260, 1115, 1080, 820, 800 $cm^{-1}$.

m/z: 538 ($M^+$), 465, 297, 250, 129, 73 (100%), 57.

Compound 11 in Table 1: 4"-[4-(1,1-Dimethylpropyloxy)butyloxy]-2,3-difluoro-4-octyloxyterphenyl Yield 0.55 g, 55% (white powder).

Transition temperatures (° C.): Cr 82.6 SmC 138.2 I.

$^1$H NMR (400 MHz) δ ($CDCl_3$): 0.84-0.92 (6 H, m), 1.14 (6 H, s), 1.29-1.35 (8 H, m), 1.44-1.56 (4 H, m), 1.71 (2 H, quintet, J 6.1), 1.80-1.93 (4 H, m), 3.38 (2 H, t, J 6.3), 4.03 (2 H, t, J 6.0), 4.08 (2 H, t, J 6.0), 6.78-6.83 (1 H, m), 6.98 (2 H, d), 7.10-7.16 (1 H, m), 7.53-7.57 (2×2 H, m), 7.63 (2 H, d).

$\nu_{max}$(KCl): 2980, 2860, 1500, 1470, 1300, 1260, 1080, 800 $cm^{-1}$.

m/z: 552 ($M^+$), 439 (100%), 409, 143.

Compound 12 in Table 1: 4"-[4-(2,2-Dimethylpropyloxy)butyloxy]-2,3-difluoro-4-octyloxyterphenyl Yield 0.64 g, 68% (white powder).

Transition temperatures (° C.): Cr 87.6 SmC 148.6 I.

$^1$H NMR (400 MHz) δ ($CDCl_3$): 0.87 (3 H, t, J 6.9), 0.91 (9 H, s), 1.29-1.35 (8 H, m), 1.43-1.52 (2 H, m), 1.76 (2 H, quintet, J 6.1), 1.84 (2 H, quintet, J 6.5), 1.91 (2 H, quintet, J 65), 3.07 (2 H, s), 3.49 (2 H, t, J 6.1), 4.05 (2 H, t, J 6.5), 4.08 (2 H, t, J 6.5), 6.78-6.84 (1 H, m), 6.98 (2 H, d), 7.10-7.16 (1 H, m), 7.52-7.59 (2×2 H, d), 7.62 (2 H, d).

$\nu_{max}$(KCl): 2970, 2880, 1610, 1495, 1475, 1260, 1120, 810 $cm^{-1}$.

m/z: 552 ($M^+$), 461, 439, 409, 143 (100%).

Compound 13 in Table 1: 4"-[4-(1,2-Dimethylpropyloxy) butyloxy]-2,3-difluoro-4-nonylterphenyl Yield 0.55 g, 55% (white powder).

Transition temperatures (° C.): Cr 55.2 SmC 114.3 I.

$^1$H NMR (400 MHz) δ ($CDCl_3$): 0.90 (6 H, dd, J 6.5), 1.03-1.11 (3 H, m), 1.21-1.42 (15 H, m), 1.64 (2 H, m), 1.71-1.79 (3 H, d, J 6.3), 1.86-1.96 (2 H, m), 2.69 (2 H, t, J 7.6), 3.13 (1 H, quintet, J 5.8), 3.41 (1 H, dt, J 6.1), 3.58 (1 H, dt, J 6.1), 4.04(2H, t, J 5.7), 6.97-7.02 (3 H, m) 7.11-7.16 (1 H, m), 7.52-7.67 (3×2 H, d).

$\nu_{max}$(KCl): 2980, 2960, 2860, 1610, 1490, 1470, 1260, 1120, 810 $cm^{-1}$.

m/z: 550 ($M^+$), 463, 408, 295 (100%), 143.

Compound 14 in Table 1: 2,3-Difluoro-4"-[4-(1-methylpropyloxy)butyloxy]-4-nonylterphenyl Yield 0.46 g, 65% (white powder).

Transition temperatures (° C.): Cr 66.1 SmC 119.0 I.

$^1$H NMR (400 MHz) δ ($CDCl_3$): 0.86-0.94 (6 H, m), 1.13 (3 H, d, J 6.4), 1.23-1.60 (14 H, m), 1.65 (2 H, quintet, J 6.4), 1.76 (2 H, quintet, J 6.8), 1.91 (2 H, quintet, J 6.7), 2.69 (2 H, t, J 7.5), 3.32 (1 H, sextet, J 6.0), 3.41-3.47 (1 H, m), 3.53-3.60 (1 H, m), 4.04 (2 H, t, J 6.5), 6.97-7.02 (3 H, m), 7.12-7.17 (1 H, m), 7.54-7.65 (3×2 H, d).

$\nu_{max}$(KCl): 2980, 2880, 1610, 1500, 1380, 1260, 1180, 1100, 800 510 $cm^{-1}$.

m/z: 536 ($M^+$), 463, 408, 379, 295, 129, 71 (100%).

Compound 15 in Table 1: 4"-[4-(1,1-Dimethylpropyloxy)butyloxy)]-2,3-difluoro-4-nonylterphenyl Yield 0.46 g, 60% (white powder).

Transition temperatures (° C.): Cr 54.7 SmC 105.7 I.

$^1$H NMR (400 MHz) δ ($CDCl_3$): 0.86-0.90 (6 H, m), 1.14 (6 H, s), 1.23-1.42 (12 H, m), 1.49 (2 H, q, J 7.5), 1.66 (2 H, quintet, J 7.4), 1.72 (2 H, quintet, J 7.4), 1.89 (2 H, quintet, J 7.4), 2.69 (2 H, t, J 7.6), 3.38 (2 H, t, 6.3), 4.04 (2 H, t, J 6.3), 6.97-7.02 (3 H, m), 7.12-7.17 (1 H, m), 7.54-7.65 (3×2 H, d).

$\nu_{max}$(KCl): 2980, 2880, 1605, 1470, 1400, 1160, 1020, 805, 500 $cm^{-1}$.

m/z: 550 ($M^+$), 463, 408 (100%), 295, 57.

Compound 16 in Table 1: 4"-[4-(2,2-Dimethylpropyloxy)butyloxy]-2,3-difluoro-4-nonylterphenyl Yield 0.46 g, 65% (white powder).

Transition temperatures (° C.): Cr 54.3 SmC 116.4 I.

$^1$H NMR (400 MHz) δ ($CDCl_3$): 0.81 (3 H, t, J 6.7), 0.84 (9 H, s), 1.15-1.36 (14 H, m), 1.57 (2 H, quintet, J 7.1), 1.69 (2 H, quintet, J 6.6), 1.83 (2 H, quintet, J 6.1), 2.62 (2 H, t, J 7.4), 3.42 (2 H, t, J 6.1), 3.98 (2 H, t, J 6.2), 6.89-6.94 (3 H, m), 7.04-7.10 (1 H, m), 7.47-7.57 (3×2 H, d).

$\nu_{max}$(KCl): 2980, 2970, 2880, 1610, 1495, 1475, 1260, 1120, 810 $cm^{-1}$.

m/z: 550 (M+), 462, 407, 295, 181, 143, 73.

EXAMPLE 9

Preparation of Compound 18 in Table 1

Step 1: Preparation of 3,7-Dimethyloctanoic Acid

A solution of chromium trioxide (55.5 g, 0.555 mol) in water (68 ml) and 2M-sulphuric acid (12 ml) was added dropwise to a solution of 3,7-dimethyloctanol (43.7 g, 0.308 mol) in acetone (100 ml), the temperature was maintained at 40-60° C. and the reaction mixture was left stirring overnight. Acetone was carefully removed in vacuo, the reaction mixture was diluted in water and washed with diethyl ether (2×200 ml). The ethereal solution was washed with 10% sodium hydroxyde solution (200 ml); and the aqueous phase was acidified with 36% HCl (200 ml) and washed once more with diethyl ether (2×200 ml). The organic layer was dried ($MgSO_4$) and the diethyl ether was removed in vacuo. The crude product was distilled to give a colourless oil.

Yield 13.60 g, 28%; bp 139-141° C. at 15 mmHg.

$^1$H NMR (270 MHz) δ ($CDCl_3$): 0.86 (6 H, d, J 6.7), 0.96 (3 H, d, J 6.8), 1.10-1.40 (6 H, m), 1.50 (1 H, m), 1.90-2.02 (1 H, m), 2.10-2.20 (1 H, s), 2.40-2.50 (2 H, m).

$\nu_{max}$(KCl): 3300-2850, 1710, 1350, 945 $cm^{-1}$.

m/z: 172 ($M^+$), 113, 97, 87 (100%).

Step 2: Preparation of 3,7-Dimethyloctanoyl Chloride

The product of step 1 (13.6 g, 0.077 mol) was heated under reflux for 1 h with thionyl chloride (13.1 g, 0.115 mol), the excess of thionyl chloride was distilled off.

Yield 13.4 g, 90%.

No attempt was made to purify the crude oil and no analyses were carried out, the product was used immediately.

Step 3: Preparation of 4-Bromo-4'-(3,7-dimethyloctyl)biphenyl

A solution of 4-bromo-biphenyl (7.00 g, 0.030 mol), aluminium chloride (4.40 g, 0.033 mol) and 3,7-dimethyloctanoyl chloride (step 2) (6.90 g, 0.036 mol), in dry DCM was prepared at room temperature. The stirring reaction mixture was left to react at room temperature until g.l.c. and t.l.c. analyses revealed a complete reaction, the reaction mixture was then treated with triethylsilane (9.30 g, 0.080 mol) and left stirring overnight. The reaction product was extracted into DCM (2×100 ml) and the combined organic layers were washed with brine, water and dried ($MgSO_4$). The product was adsorbed onto silica gel and purified by column chromatography [DCM] and recrystallised from ethanol to yield a white powder.

Yield 6.75 g, 60%; mp 88-89° C. (white powder).

$^1$H NMR (270 MHz) δ ($CDCl_3$): 0.87 (6 H, d, J 6.4), 0.96 (3 H, d, J 6.5), 1.10-1.40 (6 H, m), 1.41-1.72 (4 H, m), 2.52-2.75 (2 H, t, J 6.3), 7.24 (2 H, d), 7.40-7.58 (3×2 H, d).

$\nu_{max}$(KCl): 2980, 2940, 1490, 1470, 1080, 1000, 810, 500 $cm^{-1}$.

m/z: 374/372 ($M^+$), 258, 250/248, 245, 165, 57 (100%).

Step 4: Preparation of 4"-(3,7-Dimethyloctyl)-2,3-difluoro-4-octyloxyterphenyl (Compound 18 in Table 1)

The product of step 3 (1.00 g, 2.8 mmol), an aqueous solution of 2M-sodium carbonate (40 ml) and tetrakis(triphenylphosphine)palladium(0) (0.12 g, 0.12 mmol) were mixed in TBME (60 ml) under dry nitrogen at room temperature and 2,3-difluoroboronic acid (1.00 g, 3.5 mmol) (prepared as described in Example 1 step 4) was added. The stirred reaction mixture was heated overnight under reflux under dry nitrogen until g.l.c. and t.l.c. revealed a complete reaction. The product was extracted into DCM (2×150 ml) and washed with brine, water and dried ($MgSO_4$). The solvent was removed under reduced pressure and the residue was purified by column chromatography [DCM-hexane, 1:8] and recrystallised from hexane to give a white powder.

Yield 1.12 g, 75% (white powder).

Transition temperatures (° C.): Cr 82.5 SmC 115.3 I.

$^1$H NMR (400 MHz) δ ($CDCl_3$): 0.82-0.92 (9 H, m), 0.95 (3 H, d, J 5.9), 1.08-1.20 (2 H, m), 1.22-1.42 (11 H, m), 1.43-1.59 (6 H, m), 1.62-1.72 (1 H, m), 1.84 (2 H, quintet J 4.9), 2.52-2.74 (2 H, m), 4.08 (2 H, t, J 4.9), 6.77-6.87 (1 H, m), 7.08-7.18 (1 H, m), 7.26 (2 H, d), 7.50-7.59 (2×2 H, d), 7.65 (2 H, d).

$\nu_{max}$(KCl): 2920, 2880, 1630, 1480, 1080, 800 $cm^{-1}$.

m/z: 534($M^+$), 422, 407, 295, 57.

EXAMPLE 10

Preparation of Compounds 17, 19 and 20 in Table 1

Using a method analogous to that described in Example 9 but with the appropriate starting materials, the following compounds were prepared:

Compound 17 in Table 1: 2,3-Difluoro-4-octyloxy-4"-(3,5,5-trimethylhexyl)terphenyl Yield 1.02 g, 70%.

Transition temperatures (° C.): Cr 55.4 SmC 104.5 I.

$^1$H NMR (400 MHz) δ ($CDCl_3$): 0.85-0.97 (14 H, m), 1.00 (3 H, d, J 6.7), 1.07-1.14 (1 H, m), 1.23-1.43 (8 H, m), 1.44-1.70 (4 H, m), 1.88 (2 H, quintet, J 6.5), 2.57-2.73 (2 H, m), 4.07 (2 H, t, J 6.5), 6.78-6.85 (1 H, m), 6.97-7.03 (1 H, m), 7.25 (2 H, d), 7.52-7.66 (3×2 H, d).

$\nu_{max}$(KCl): 2980, 2880, 1640, 1500, 1480, 1300, 1080, 800 $cm^{-1}$.

m/z: 520 ($M^+$), 408 (100), 295, 57.

Compound 19 in Table 1: 2,3-Difluoro-4-nonyl-4"-(3,5,5-trimethylhexyl)terphenyl

Yield 1.00 g, 70% (white powder).

Transition temperatures (° C.): Cr 53.7 SmC 62.7 I.

$^1$H NMR (400 MHz) δ ($CDCl_3$): 0.87-0.94 (12 H, m), 1.00 (3 H, d, J 6.2), 1.08-1.14 (1 H, m), 1.27-1.35 (14 H, m), 1.43-1.59 (4 H, m), 2.57-2.72 (4 H, m), 6.97-7.02 (1 H, m), 7.07-7.17 (1 H, m), 7.27 (2 H, d), 7.53-7.68 (3×2 H, d).

$\nu_{max}$(KCl): 2980, 2880, 1500, 1460, 1400, 1120, 800 $cm^-$.

m/z: 518 ($M^+$), 391 (100%).

Compound 20 in Table 1: 4"-(3,7-Dimethyloctyl)-2,3-difluoro-4-nonylterphenyl

Yield 1.10 g, 70% (white powder).

Transition temperatures (° C.): Cr 28.2 SmC 75.2 I.

$^1$H NMR (400 MHz) δ ($CDCl_3$): 0.86 (9 H, m), 0.94 (3 H, d, J 5.7), 1.09-1.20 (2 H, m), 1.22-1.42 (18 H, m), 1.43-1.58 (2 H, m), 1.62-1.72 (2 H, m), 2.58-2.74 (4 H, m), 6.77-6.87 (1 H, m), 7.08-7.18 (1 H, m), 7.27 (2 H, d), 7.55 (2 H, d), 7.59 (2 H, d), 7.66 (2 H, d).

$\nu_{max}$(KCl): 2980, 2880, 1500, 1080, 900, 800 $cm^{-1}$.

m/z: 532 ($M^+$), 422, 407, 295, 57.

Liquid Crystal Properties

The liquid crystal properties of the compounds of the invention were tested using conventional methods. In particular the melting and clearing points of compounds of the invention were compared with a structurally similar compound. In this case, the comparative compound is shown in Table 2.

TABLE 2

| Comparative Example | Structure |
| --- | --- |
| B | 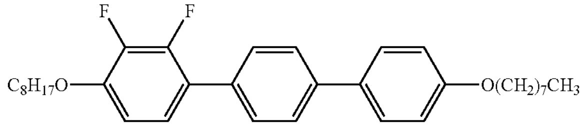 |

The compound included in this test were related to comparative compound B in that they all dialkoxy compounds and have a similar chain length but with different end groups.

Compound B has the same number of atoms along its terminal chain (nine), but no bulky end group (only a straight alkoxy chain).

Compound 1 has the same chain length (nine).

Compound 2 is related to compound 1 in that it has the same number of carbon atoms in the terminal chain but one methyl group is moved from the end of the chain to the fourth atom.

The transition temperatures of these compounds was measured and is given in Table 3.

TABLE 3

| Compounds | Cr | | SmC | | N | | I |
|---|---|---|---|---|---|---|---|
| | Transition temperatures (° C.) and enthalpies of transitions (J $g^{-1}$) | | | | | | |
| 2 | • | 82.5 [33.4] | • | 132.2 | • [10.4]* | 138.0 | • |
| B | • | 114.8 [42.6] | • | 175.8 | • [14.9]* | 178.1 | • |
| 1 | • | 97.3 [26.1] | • | 160.1 [17.9] | — | — | • |

*ΔH value for the I to SmC transition

The comparison of the values for compound B with those for compound 1 which contains a tert-butyl end group, shows that the bulky end group has reduced the melting point by 17.5° C. and the clearing point by 18.0° C. Compound 1 shows only a smectic C phase; the smectic C phase has been suppressed, but to a lesser extent than for the nematic phase.

Compound 1 has a lower melting point (17.5° C.) and clearing points (18.0° C.) than for compound B with an unbranched terminal chain. Compound 2 has a lower melting point and a much lower clearing point than compound 1 (14.8 and 22.1° C. respectively), showing that the methyl group on the fourth atom has a much greater effect on the depression of the clearing point than a terminal methyl branching. The current comparison of compounds 2 and 1 is effectively showing two different positions of methyl substitution in a chain ending in an isopropyl unit. Compound 1 only shows a smectic C phase. The methyl substituent at the fourth atom in the terminal chain gives a compound which allows a nematic phase to exist whereas the bulkier end group in compound 1 is more conducive to the smectic C phase.

Further comparisons were made with alkyl alkoxy systems. In this case a different comparison compounds were used as shown in Table 4.

Compound 3

| | | | | | | |
|---|---|---|---|---|---|---|
| Cr | 60.4 | SmC | 126.5 | I | (° C.) |
| ΔH | [18.7] | | [16.6] | | (J g−1) |

Compound D with two straight chain terminal groups shows a smectic A, a smectic C, a smectic I and a crystal J phase, whereas compound 3 shows only the SmC phase. The branched chain compound (3) has a slightly lower melting points (2.7° C.) and rather more greatly depressed clearing point (22.4° C.) than the straight chain analogue compound D.

In conclusion, the bulky end groups in these series of compounds have several effects on the overall mesomorphic properties of the compounds. The effects that have been observed for the dialkoxy and alkyl-alkoxy series are:

The bulky end group reduces the melting and the clearing point and acts to hinder the packing and the molecular association of the molecules.

The bulkier the end group the greater the effect on the melting point and on the clearing point.

The liquid crystalline temperature range was not significantly affected by the presence of the bulky end group. Compound B has a liquid crystal range of 63.3° C., and compound 1 has a liquid crystal range of 62.8° C.

The only mesophase displayed by the materials reported, is the smectic C phase. This observation suggests that the bulky end group, because of its steric hindrance, depresses the mesophase stabilities but it suppresses the nematic and the smectic A phases more than the smectic C phase.

Compound 5 was used to study the effect of a cyclobutyl end group on the mesomorphism of a difluoroterphenyl core and also to study its miscibility with a standard smectic C material. The cyclobutyl unit is similar to, but less spatially demanding than, an isopropyl end group.

TABLE 4

| Comparative Example | Structure |
|---|---|
| D | 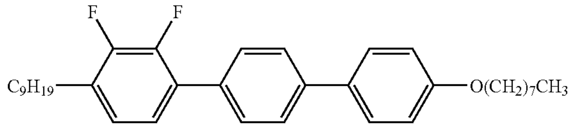 |

Compound D has the same number of atoms along its terminal chain (nine) as Compound 3, but no bulky end group (only a straight alkoxy chain).

The results are set out below

Compound D

| | | | | | | | | | | | |
|---|---|---|---|---|---|---|---|---|---|---|---|
| Cr | 63.1 | Cryst J | 68.9 | SmI | 79.6 | SmC | 90.2 | SmA | 148.9 | I | (°C.) |
| ΔH | [28.7] | | [1.34] | | [15.2] | | [3.10] | | [17.0] | | (Jg-1) |

Compound 6 containing a methyl-substituted oxetane ring as an end group was prepared for comparison with compound 5; the oxetane unit is similar to a t-butyl group and has the unusual property of an oxygen atom as the outermost component of the chain.

Compound 5

| | | | | | |
|---|---|---|---|---|---|
| Cr | 92.5 | SmC | 148.1 | I | (° C.) |
| ΔH | [24.5] | | [17.7] | | ($Jg^{-1}$) |

Compound 6

| | | | | | | | |
|---|---|---|---|---|---|---|---|
| Cr | 97.7 | SmC | 124.8 | N | 137.8 | I | (° C.) |
| ΔH | [14.5] | | [0.13] | | [0.58] | | ($Jg^{-1}$) |

Compound 6 and compound 5 have similar melting points but compound 6 shows a nematic phase as well as the smectic C phase, whereas compound 5 only shows a smectic C phase. The stability of the smectic C phase in compound 6 is suppressed and the nematic phase is favoured by the presence of the oxygen atom and the methyl substituent.

Two series of compounds, 7-12 and 13-16 for the octyloxy and nonyl systems respectively, were compared with a further comparative Example G of structure:

G

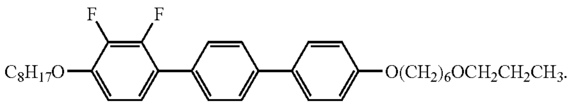

This allowed comparison in relation to the presence of branching near the end of a nine atom chain. The compounds had end groups of varying size so that the effect of bulkiness on the mesophase transitions and melting points could be compared. Compounds G and 7-12 and 13-16 differ in the presence and position of various methyl groups in the chain at the 4"-position. The results are shown in Tables 6 and 7.

TABLE 6

| Transition temperatures for compounds (° C.) and enthalpies of transitions (J $g^{-1}$) | | | | | | | | |
|---|---|---|---|---|---|---|---|---|
| Compounds | Cr | | SmC | | N | | I | |
| G | • | 104.5 [32.3] | • | 158.8 | • | 162.3 [13.2]* | • | |
| 7 | • | 84.5 [16.2] | • | 142.8 [14.5] | — | — | • | |
| 8 | • | 88.7 [15.4] | • | 139.4 [15.6] | — | — | • | |
| 9 | • | 99.7 [30.5] | • | 155.5 [15.4] | — | — | • | |
| 10 | • | 92.0 [14.5] | • | 148.7 [13.8] | — | — | • | |
| 11 | • | 82.6 [16.3] | • | 138.2 [15.3] | — | — | • | |
| 12 | • | 87.6 [17.5] | • | 148.6 [16.4] | — | — | • | |

*ΔH value for the I to SmC transition

Molecular Volumes and End Group Volumes of Compounds G and 7-12

| Compounds | Molecular volume/$Å^3$ | End group volume/$Å^3$ |
|---|---|---|
| G | 542.50 ± 5.40 | 69.15 ± 3.10 |
| 7 | 583.45 ± 4.10 | 106.20 ± 1.35 |
| 8 | 597.20 ± 5.20 | 124.70 ± 2.15 |
| 9 | 554.10 ± 3.15 | 88.10 ± 1.00 |
| 10 | 561.50 ± 3.20 | 88.70 ± 0.95 |
| 11 | 582.40 ± 4.80 | 105.10 ± 2.80 |
| 12 | 584.95 ± 4.40 | 105.15 ± 1.90 |

Compound G is the straight chain reference compound for this study and is the only material that displays a nematic phase and a smectic C phase. All the other compounds in the series only show the smectic C phase. The mesophase range is retained when bulkiness is varied and branching by methyl groups in the chain occurs at different positions.

The series G, 9 and 10 shows the effect of moving a methyl substituent from near the end position to a point closer to the mesogenic core. This sequence gives a gradual decrease in clearing and melting points.

Compounds 11 and 12 have two methyl groups attached to the same carbon atom but they differ in the position of attachment along the chain. Compound 12 is a tert-butyl group. Compound 11 has a lower melting point and clearing point than compound 12 (5 and 10.4° C. respectively). This difference conforms to the effects seen for compounds G, 9 and 10 on moving the substituent closer to the core.

As with compounds 11 and 12, compound 7 has two methyl substituents, but the two methyl groups are not at the same position in the chain. Compound 7 has a lower melting point and a lower clearing point than compound 12 (3.1 and 5.8° C. respectively) but has a higher melting point and higher clearing point than compound 11 (1.9 and 4.6° C. respectively); once again these effects are consistent with those noted above.

Compound 8 has three methyl substituents present and is related to compounds 7 and 12; in these cases the generalities detected for mono- and di-methyl substitution are not maintained. Compound 8 has a higher melting point and a lower clearing point than compound 7 (4.2 and 3.4° C. respectively) and it has a higher melting point and a lower clearing point than compound 12 (1.1 and 9.2° C. respectively).

In general, but with the exception of compound 8, the more methyl groups that are present and the closer they are to the core, the lower are the melting and clearing points. As seen in this series, introducing bulkiness supresses the nematic phase and only the straight chain compound G shows the nematic phase.

Figure 2:
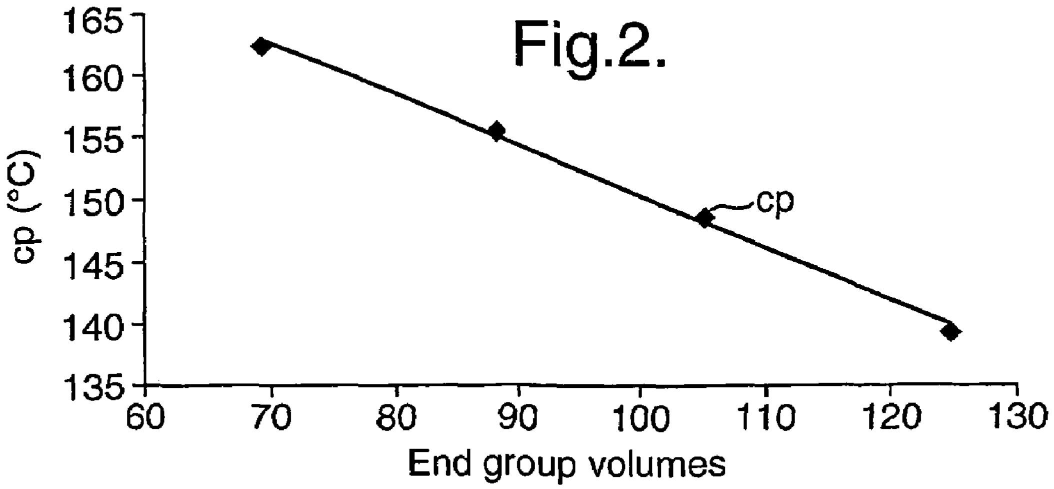
FIG. 2 is a graph showing clearing points vs end group volumes for compounds G, 8, 9 and 12 hereinafter.

Values of the molecular and end group volumes including the oxygen atom were determined using the Cerius$^2$ (version 1.5) software on a silicon graphics workstation. Generally, it seems that the the greater the volume, then the higher is the depression of clearing points and melting points. This is shown by FIGS. 1 and 2 which plots an apparently linear depreciation in the melting and clearing points in respect of compounds G, 8, 9 and 12. In this series the substitution occurs at the same carbon centre (G, 9 and 12) and compound 8 has the same methyl substitution as compound 12 but one methyl substituent at the 7-position in the chain.

Compounds 15 and 16 have two methyl substituents on the same carbon atom but they differ in the position of substitution in the chain. Both compounds have a similar melting point but compound 15 with the substituents closer to the core has a significantly lower clearing point than compound 16 (10.7° C. respectively).

Compound 13 has a lower melting point and clearing point than compound 14 and this is consistent with the additional methyl substituent in compound 13. The results for these compounds is shown in Table 9.

TABLE 9

| Compounds | Cr | Transition temperatures (° C.) and enthalpies of transitions (J $g^{-1}$) | SmC | | I |
|---|---|---|---|---|---|
| 13 | • | 55.2 [20.6] | • | 114.3 [13.0] | • |
| 14 | • | 66.1 [13.4] | • | 119.0 [13.8] | • |
| 15 | • | 54.7 [31.6] | • | 105.7 [20.5] | • |
| 16 | • | 54.3 [14.4 | • | 116.4 [13.3]] | • |

The transition temperatures for these two series of compounds suggest the following conclusions.

The alkyl-alkoxy series has lower melting and lower clearing points than their dialkoxy analogues.

The greater the steric volume the lower the melting and clearing point.

The position of the substitution in the chain is important; the clearing point is greater when the branching is closer to the mesogenic core.

The bulky end group suppresses the nematic phase.

Compounds 17-20 were compared to investigate the effects of bulky end groups in conjunction with methyl branching in the chain for alkoxy-alkyl compounds (17 and 18) and dialkyl compounds (19 and 20) (see Table 10).

TABLE 10

| Compounds | Cr | Transition temperature (° C.) and enthalpies of transitions (J $g^{-1}$) | SmC | | I |
|---|---|---|---|---|---|
| 17 | • | 55.4 [15.0] | • | 104.5 [11.9] | • |
| 18 | • | 82.5 [36.9] | • | 115.6 [13.5] | • |
| 19 | • | 53.7 [27.9] | • | 62.7 [8.95] | • |
| 20 | • | 28.2 [13.3] | • | 75.2 [10.5] | • |

Once again, compounds in this series only show the smectic C phase; all the examples have a methyl substituent at the 3-position in the chain, but compounds 17 and 19 have six atoms along the chain whereas compounds 18 and 20 have eight atoms along the chain. Compound 17 has a lower melting and clearing point than compound 18 (27.1 and 11.1° C. respectively); these results might be explained by the fact that compound 17 possesses the shorter chain and the bulkier end group (t-butyl compared to isopropyl for compound 18).

The compounds shown in table 10 have the same relationship of clearing points (compounds 17 and 19 have lower clearing points than compounds 18 and 20 respectively) but compound 19 has a higher melting point than 20, whereas compound 17 has a lower melting point than 18. The results for compounds 20 and for compound 18 arise from a combination of two factors and show that a greater smectic C mesophase stability is achieved with longer chains and a less bulky end group.

Liquid Crystal Properties of Mixtures

Two assessments of the miscibility of compounds with bulky end groups were carried out. Firstly, a series of mixtures were prepared to assess whether compounds containing bulky end groups are miscible with compounds with straight alkyl chains; the mesophases and the transition temperatures produced in these mixtures are given in Table 11 for accurate compositions which are close to 20% by weight of each compound in the host. The host compound chosen for the mixture work was MH 198, which is typical of components in the difluoroterphenyl ferroelectric host systems produced at DERA (Malvern). The structure of MH 198 is

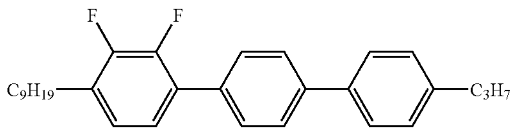

MH198

All the compounds were found to be miscible with MH 198 which suggests that they are probably miscible with other similar straight alkyl chain terphenyls.

TABLE 11

| Compound % in MH198 | Cr | Transition temperatures (° C.) for mixtures of compounds of the invention in MH198 (the change in each transition temperature from the value for the host is given in parenthesis) | SmC | | SmA | | N | | I |
|---|---|---|---|---|---|---|---|---|---|
| 1 19% | • | 53.3 (−26.7) | • | 98.8 (+14.3) | • | 132.2 (+15.2) | • | 135.5 (+4.0) | • |
| 3 20% | • | 54.2 (−25.8) | • | 87.0 (+2.5) | • | 127.6 (+10.6) | • | 130.5 (−1.0) | • |
| 5 20% | • | 55.6 (−24.4) | • | 97.8 (+13.3) | • | 123.9 (−6.9) | • | 134.0 (+2.5) | • |
| 6 19% | • | 54.1 (−25.9) | • | 89.7 (+5.2) | • | 117.8 (+0.8) | • | 131.1 (−0.4) | • |

Tables 11 shows that the melting points are down as expected in a mixture. The transition temperatures of smectic C and A phases are nearly always increased and the transition temperatures of the nematic to isotropic are unchanged.

Figure 3:
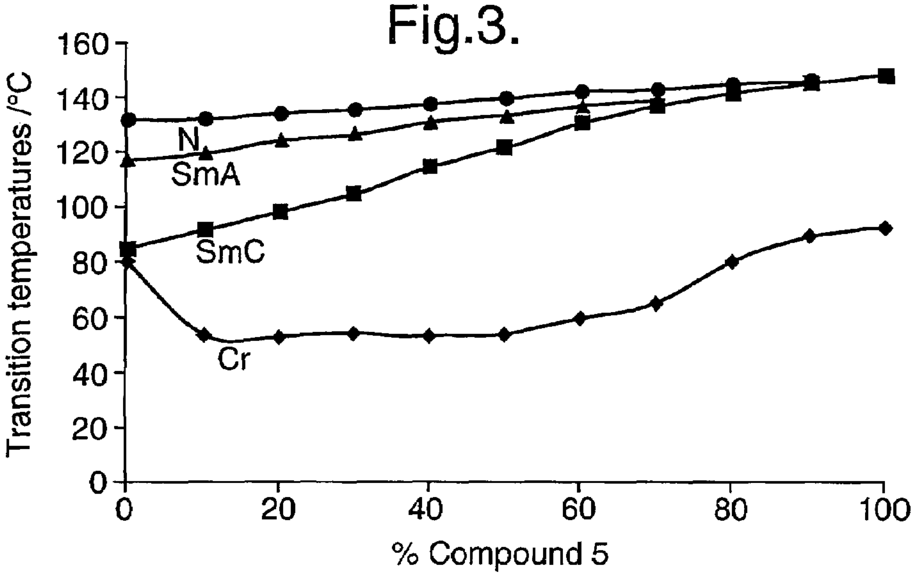
FIG. 3 is a binary phase diagram for mixtures of 5 and MH 198.

In the second assessment of miscibility, compound 5 (with an octyloxy chain) was mixed with compound MH 198 in all proportions, and the transition temperatures are given in Table 12. The binary miscibility diagram is shown in FIG. 3 and does not show any discontinuity across the phase diagram. These compounds containing bulky end groups in their terminal chains are miscible with similar compounds containing straight terminal chains, and this suggests that the compounds with the bulky end groups do not microsegrate on mixing with the straight chain analogues. (This result is different from that reported by Coles and co-workers for siloxane end groups which give microsegrated regions)

Although compound 5 does not possess either a smectic A or a nematic phase, the miscibility diagrams show that these compounds are quite supportive of the smectic A and of the nematic phases in mixtures. The smectic A and the nematic phase transitions do not drop to lower values but are maintained across the diagram until they are dominated by the smectic character of the additives.

TABLE 12

Transition temperatures (° C.) for mixtures of compound 5 and MH 198

| % of 1 in MH 198 | Cr | | SmC | | SmA | | N | | I |
|---|---|---|---|---|---|---|---|---|---|
| 10 | • | 53.3 | • | 91.5 | • | 119.4 | • | 131.8 | • |
| 20 | • | 52.6 | • | 97.8 | • | 123.9 | • | 134.0 | • |
| 30 | • | 53.9 | • | 104.5 | • | 126.1 | • | 135.2 | • |
| 40 | • | 52.9 | • | 114.3 | • | 130.7 | • | 137.5 | • |
| 50 | • | 53.6 | • | 121.4 | • | 133.2 | • | 139.2 | • |
| 60 | • | 59.5 | • | 130.7 | • | 136.5 | • | 141.6 | • |
| 70 | • | 65.0 | • | 136.7 | • | 138.6 | • | 142.6 | • |
| 80 | • | 79.9 | • | 141.3 | — | — | • | 144.6 | • |
| 90 | • | 89.5 | • | 145.1 | — | — | • | 146.2 | • |
| 100 | • | 92.5 | • | 148.1 | — | — | — | — | • |

Electro-optical Studies of Bulky end Groups in a Standard Mixture

Figure 4:
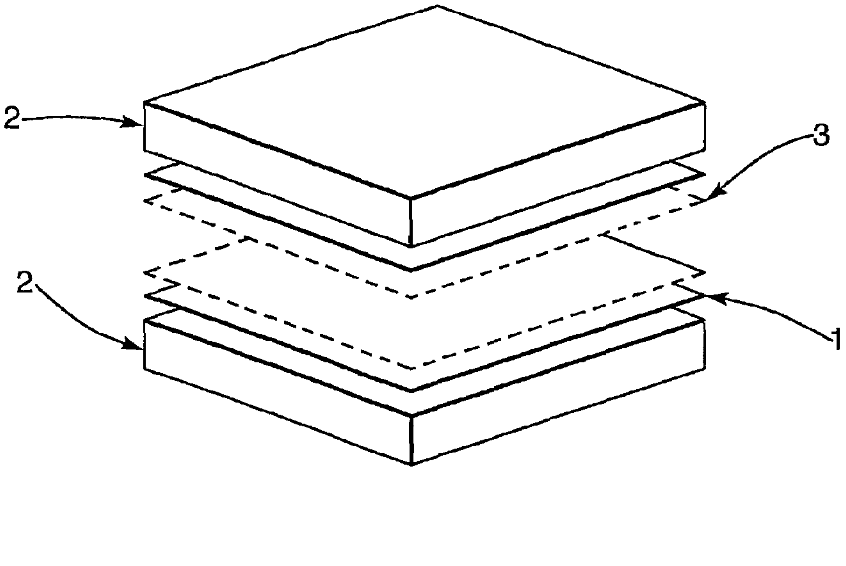
FIG. 4 is an exploded view of a cell used for electro-optical studies.

A compound of the invention and some comparative compounds were mixed in a standard ferroelectric mixture used at DERA (Malvern) to determine the magnitude of their Ps, their tilt angle and the switching times as a function of temperature. The Ps and tilt angle measurements were carried out in 5 μm cells filled by capillary action as described below, and the switching time measurements were carried out in 1.2 μm cells. The cells used were coated with a parallel-rubbed polyimide alignment layer. FIG. 4 shows an exploded view of a typical cell which consists of three parts—ITO electrodes (1), glass substrates (2) and spacers (3).

The method used to fill the cell was to allow the material to flow into the cell at a temperature approximately 10° C. above the clearing point in a vacuum oven. The 5 μm cells (for Ps and tilt angle measurements) were placed in a Linkam cell holder (THMS/LCC) which provided a connection to electrodes for the application of an electric field. The 1.2 μm cells (for the switching time studies) were filled and coated with a conductive silver paste on top and bottom to provide a connection to electrodes for the application of an electric field. The cell was placed directly in the heating stage (THM600) on a Zeiss microscope; the heating stage was controlled by the Linkam TP61 temperature controller.

In order to align the materials homogeneously, the liquid crystal sample was cooled from the isotropic liquid into the SmC* phase via the N* and SmA* phases. Several conditions were tried to obtain optimum alignment in the cells and the best procedure was as follows, a frequency of 200 Hz was applied and a voltage of ±10 V (2 V $\mu m^{-1}$ for the 5 μm cells and ±8.5 V $\mu m^{-1}$ for the 1.2 cells) with a cooling rate of 0.2° C. min-$^{1}$.

The DFT1 mixture is composed of the following compounds (% by weight):

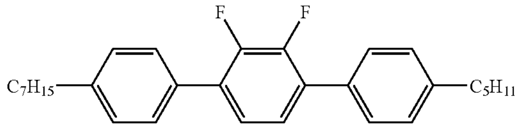

50%

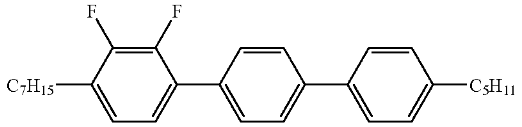

25%

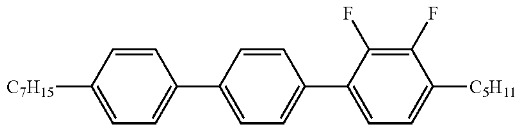

25%

CSmix (Chiral Standard mixture) DFT1 mixture with 2% by weight of BE8OF2N dopant was prepared, to which 25% by weight of a bulky end group compound was added. The chiral dopant BE8OF2N had the formula

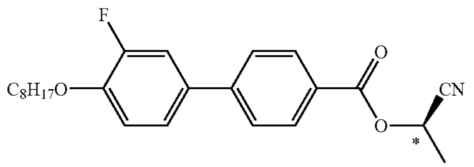

BE8OF2N

The aim of the electro-optic study was to compare the effect of a bulky end group on the switching time of the standard CSmix mixture. Each mixture tested contains 25% of a bulky end group material, but only a few materials were tested due to the great difficulty in aligning the sample in the cells. The materials chosen for this study are as follows, Compound B is a reference compound with a straight alkoxy chain.

Compound 1 of the invention.

Mixture II contained 25% of compound B (See Table 2).

Mixture III contained 25% of compound 1 in Table 1.

Procedures for Ps Measurements—Triangular Wave Studies

The Ps value was measured by the application of an AC driving voltage using a triangular waveform to an aligned SmC* sample; this method is also known as current reversal. Since the dipoles in the medium tend to align perpendicular to the plane of the glass plates, it is possible to directly couple the Ps of the medium to the applied electric field. In a ferroelectric phase, the molecules will rapidly reorient themselves from one aligned state into another aligned state by switching around a cone and so give rise to a brief pulse of current which is detected as a single peak.

The cell was placed in the Linkam cell holder, and the cell holder was connected to the electronic wave generator and inserted into the THM600 Linkam heating stage on a Zeiss microscope. An AC driving voltage using a triangular waveform was applied so that when the electrical field started to rise in the cell, at a certain point the dipoles would align with the field and the aligned sample would switch. An oscilloscope measured the resulting current, I, from the cell and showed a peak (current pulse) which represents the spontaneous polarisation.

The Ps values for all the mixtures was determined by the triangular wave method as 2.0±0.2 nC $cm^{-2}$ when fully saturated and did not vary for different materials. The presence or nature of the bulky end group did not seem to affect the Ps of the ferroelectric mixture.

Tilt Angle Measurements

The tilt angles of the aligned samples were measured by applying a driving voltage using a square waveform across the cell at the same voltage as for the Ps measurements but at a much lower frequency, (typically 10 MgZ) to determine the point of extinction. Once the switching had occurred, the sample was rotated through the minimum angle in order to obtain optical extinction again. This measurement gave the cone angle 2θ, where θ is the tilt angle.

As was the case for the Ps measurements, the tilt angles for all the mixtures at various temperatures were similar 22.5-23.5°.

Each mixture was placed in a 2 μm cell and the voltage applied was 10 V peak-to-peak at a frequency of 100 Hz. A photodiode (RS303-674; 1 $cm^2$ active area, high speed>50 ns) in an apparatus designed at DERA, Malvern, detected the difference in the transmission of light through the cell as the molecules changed their orientation in response to the applied electric field. A green eye response filter (Coherent-Ealing, 26-7617-000, 1" diameter, transmittance 400-700 nm, maximum transmittance 539.5 nm) was used to remove any UV and IR radiations that may have affected the results. The photodiode was linked to the oscilloscope and a signal which represented the delayed switching of the molecules within the cell was produced. It was possible to measure the response time in both directions and this is reported as the rise time (0-90% transmission) and the fall time (100-10% transmission). The switching times were reported in μs.

The rise times and fall times of Mixtures II and III were obtained by the method described above to study the effect of a bulky end group on the switching times of the standard CSmix mixture. The results are shown below in Tables 14 and 15.

TABLE 14

Rise time and fall time values for Mixture II

| Reduced Temperature*/° C. | Rise Time/μs | Fall Time/μs |
|---|---|---|
| 5 | 444 | 448 |
| 10 | 520 | 532 |
| 15 | 590 | 596 |
| 20 | 694 | 690 |
| 25 | 790 | 720 |
| 30 | 870 | 750 |
| 35 | 920 | 780 |
| 40 | 1020 | 740 |

TABLE 14-continued

Rise time and fall time values for Mixture II

| Reduced Temperature*/° C. | Rise Time/μs | Fall Time/μs |
|---|---|---|
| 45 | 1080 | 790 |
| 50 | 1210 | 820 |
| 55 | 1230 | 1000 |
| 60 | 1290 | 1030 |

*($T_c$ − T)

TABLE 15

Rise time and fall time values for Mixture III

| Reduced Temperature*/° C. | Rise Time/μs | Fall Time/μs |
|---|---|---|
| 5 | 424 | 416 |
| 10 | 480 | 460 |
| 15 | 500 | 480 |
| 20 | 560 | 520 |
| 25 | 612 | 560 |
| 30 | 660 | 660 |
| 35 | 750 | 680 |
| 40 | 840 | 704 |
| 45 | 940 | 820 |
| 50 | 1100 | 870 |
| 55 | 1130 | 890 |

*($T_c$ − T)

Mixture II switches slower than Mixture III down to 30° C. into the smectic C phase but is faster below that temperature. The rise and fall times run parallel to each other for Mixture III, but for Mixture II the fall time is faster when more than 25° C. into the smectic C phase.

Mixture III which includes a compound of the invention is faster than Mixture II and its rise and fall times run parallel down to 30° C. into the smectic C phase and then is faster than its rise time.

Bulky end groups, (as judged from these 25% mixtures) seem to give faster switching than Mixture II.

τ/Vmin Measurements

In order improve the full bistability and eliminate crosstalk in conventional FLC displays which subsequently reduce contrast, an AC field of high frequency can be applied (see section 1.7.3.1) as it will couple to the dielectric tensor without coupling to the Ps vector to maintain the transmission in the maximum or minimum desired states.

The τ/Vmin measurements at two different temperatures of 25 and 48° C. into the smectic C phase. Usually measurements are carried out at 25° C. into the smectic C phase and at 25° C., but it was not possible to make the measurements at 25° C. in these cases as the mixtures recrystallised at about 30° C. The equipment used consisted of a Nikon Optiphot polarising microscope, Mettler FP82 heating stage in conjunction with a FP80HT temperature controller, a feedback function generator F6601A, and an in-house built photodiode assembly and an amplifier (×10) wave form generator (Wavetek Generator 395) and a Gould oscilloscope model 4072A. The measurements were taken in a 1:100 duty cycle multiplexing waveform applied from the arbitrary function generator, and the τ/V curves were obtained with a superimposed square wave AC of 50 kHz frequency. The measurements were started at a RMS of 5 V and continued at 2.5 V increments. When the onset of defects was noticed, the measurements were stopped and the cell was realigned. The cells used and alignment techniques used were identical to those used for the switching studies. The results are shown in Tables 16 and 17.

TABLE 16

Times (μs) for the switching vs voltage for Mixture II, Mixture III at 25° C. into the Smectic C* phase.

| Volt | Mixture II | Mixture III |
|---|---|---|
| 5 | 132 | 114 |
| 7.5 | 59 | 51 |
| 10 | 43 | 32 |
| 12.5 | 29 | 24 |
| 15 | 23 | 19 |
| 17.5 | 19 | 14 |
| 20 | 17 | 9 |
| 22.5 | 15 | 9 |
| 25 | 12 | 7 |

TABLE 17

Times (μs) for the switching vs voltage (V) for Mixtures II and III 48° C. into the smectic C* phase

| Volt | Mixture II | Mixture III |
|---|---|---|
| 5 | 798 | 407 |
| 7.5 | 323 | 230 |
| 10 | 130 | 140 |
| 12.5 | 65 | 52 |
| 15 | 44 | 37 |
| 17.5 | 36 | 30 |
| 20 | 28 | 25 |
| 22.5 | 24 | 21 |
| 25 | 22 | 19 |

*Could not be determined

The results show that in this mode, Mixture III requires a lower voltage than Mixture II to achieve the same switching speed i.e. mixtures containing a bulky end group compound are faster than the mixture containing a straight chain compound. These results are true for both at 25 and 48° C. into the chiral smectic C phase.

All the measurements reported above, were not obtained for neat materials, but only for materials as a mixture in a host, and so the results should only be regarded qualitatively. However, a conclusion that can be drawn from these results is that a bulky end group clearly affects the switching times to give faster switching times than for materials without a bulky group (see Mixture II). The reason for the faster switching probably arises more from the steric effects on the interlayer mixing process than from the intrinsic nature of the bulky end groups.

All the results in this section suggest that the mixtures containing compounds with a bulky end group have faster switching times than the non-bulky end group mixtures and that, within the range of end groups considered here, the particular nature of the bulky end group has no specific effect on the switching times other than its steric hinderance. The switching process is probably enhanced because the terminal groups with bulky ends do not intermix as effectively in the interlayer region and so the molecules are able to switch faster from one bistable state to the other because the terminal groups do not need to be disentangled. The tilt angles of the mixtures were affected by the presence of the bulky end groups.

The invention claimed is:

1. A method of decreasing the melting point, increasing the clearing point, increasing the speed of switching and/or increasing the tilt angle of a liquid crystal mixture, which comprises adding to the mixture a mesogenic compound of formula (I)

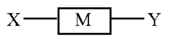

(I)

having a terminal end chain (X,Y) comprising carbon, oxygen or sulphur, which has at least one pendent $C_{1-4}$ alkyl or $C_{1-4}$ alkoxy groups, or a cycloalkyl or cycloalkoxy ring, arranged no more than 6 atoms from the end of the chain wherein M is a mesogenic core group, and X and Y are selected from a functional group, an optionally substituted alkyl chain, an optionally substituted alkenyl chain, an optionally substituted alkynyl chain or a group of sub-formula (i), provided that at least one of X or Y is a group of sub-formula (i)

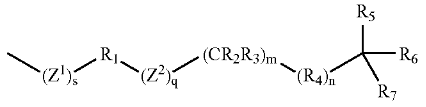

(i)

where $R_1$ is an alkylene chain optionally interposed with one or more oxygen or sulphur atoms;

$Z^1$ and $Z^2$ are independently selected from oxygen or sulphur;

s and q are independently selected from 0 or 1;

m is 1;

$R_2$, $R_3$, $R_5$ and $R_6$ are independently selected from hydrogen, $C_{1-4}$alkyl, $C_{1-4}$alkoxy; or $R_5$ and $R_6$ or $R_2$ and $R_3$ together with the carbon atom to which they are attached form a $C_{3-7}$cycloalkyl or $C_{3-7}$cycloalkoxy group, provided that at least one of the groups $R_2$, $R_3$, $R_5$ and $R_6$ is other than hydrogen, n is 0 or an integer of from 1 to 4, and each group $R_4$ is independently selected from oxygen, sulphur or a group $CR_8R_9$ where $R_8$ and $R_9$ are independently selected from hydrogen, $C_{1-4}$alkyl or $C_{1-4}$alkoxy; and $R_7$ is hydrogen or methyl, provided that where $R_7$ is methyl, n is other than 4, further provided that neither $R_2$ nor $R_3$ are hydrogen when only one of X or Y is a group of sub formula (i) or when $R_6$ and $R_7$ do not form a $C_{3-7}$cycloalkyl or $C_{3-7}$cycloalkoxy group.

2. The method according to claim 1, wherein in the compound of formula (I), X and Y are the same or different but are both groups of sub-formula (i).

3. The method according to claim 1, wherein in the compound of formula (I), at least two of $R_2$, $R_3$, $R_5$ and $R_6$ are other than hydrogen.

4. The method according to claim 1, wherein s is 1 and $R_1$ is a group of sub formula (ii), $$-(CH_2)_p-(O)_s- \quad \text{(ii)}$$

where p is an integer of from 2 to 10.

5. The method according to claim 1, wherein in the compound of formula (I), the group of formula (i) is a group of sub-formulae (iii) or (iv)

(iii)

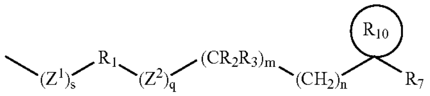

(iv)

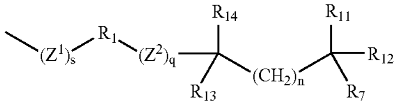

where $Z^1$, $Z^2$, $R_1$, $R_2$, $R_3$, $R_7$, s, q, m and n are as defined in claim 1, $R_{10}$ is a $C_{3-7}$ cycloalkyl or $C_{3-7}$ cycloalkoxy group, $R_{11}$ and $R_{12}$ are independently selected from hydrogen or $C_{1-3}$alkyl, $R_{13}$ is methyl, and $R_{14}$ is $C_{1-3}$alkyl.

6. The method according to claim 2, wherein in the compound of formula (I), the group of formula (i) is a group of sub-formulae (v), (v)

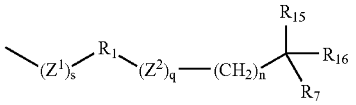

where $Z^1$, $Z^2$, $R_1$, $R_7$, s, q, m and n are as defined in claim 1, $R_{15}$ is hydrogen or $C_{1-3}$alkyl, and $R_{16}$ is $C_{1-3}$alkyl, provided X and Y are the same or different but are both groups of sub-formula (i).

7. The method according to claim 1, wherein in the compound of formula (I), the mesogenic groups M is a group of formula (II), $$-(R_{17}-W_1)_f-(R_{18}-W_2)_g-(R_{19})- \qquad \text{(II)}$$

where $R_{17}$, $R_{18}$ and $R_{19}$ are independently selected from cycloalkyl, aryl or heterocyclic rings, any of which may be optionally substituted by one or more groups selected from halo, $C_{1-5}$alkyl, cyano, $C_{1-5}$alkoxy or NCS;

$W_1$ and $W_2$ are independently selected from a direct bond, —C(O)O —, —OC(O)—, —$CH_2$—, —$CH_2CH_2$—, —$CH_2O$—, —$OCH_2$—, —O—, —S—, —CH═CH—, or —C≡C—;

f is 1 or 2, g is O, 1 or 2, provided that f+g does not exceed 3.

8. The method according to claim 7, wherein in formula (II), $R_{17}$, $R_{18}$ and $R_{19}$ are independently selected from phenyl and cyclohexyl rings, which may be optionally substituted.

9. A method of improving the melting or clearing point of a liquid crystal compound or mixture, which comprises adding to the mixture a mesogenic compound of formula (I) as defined in claim 1.

* * * * *